(12) United States Patent
Baroja Fernandez et al.

(10) Patent No.: US 8,168,856 B2
(45) Date of Patent: May 1, 2012

(54) METHOD OF PRODUCTION OF RECOMBINANT SUCROSE SYNTHASE, USE THEREOF IN THE MANUFACTURE OF KITS FOR DETERMINATION OF SUCROSE, PRODUCTION OF ADPGLUCOSE AND PRODUCTION OF TRANSGENIC PLANTS WHOSE LEAVES AND STORAGE ORGANS ACCUMULATE HIGH CONTENTS OF ADPGLUCOSE AND STARCH

(75) Inventors: Miren Edurne Baroja Fernandez, Edificio el Sario (ES); Francisco José Muñoz Perez, Edificio el Sario (ES); Francisco Javier Pozueta Romero, Edificio el Sario (ES); Maria Teresa Moran Zorzano, Edificio el Sario (ES); Nora Alonso Casajus, Edificio el Sario (ES)

(73) Assignees: Universidad Publica de Navarra, Pamplona, Navarra (ES); Consejo Superior de Investigaciones Cientificas, Madrid (ES)

( * ) Notice: Subject to any disclaimer, the term of this patent is extended or adjusted under 35 U.S.C. 154(b) by 962 days.

(21) Appl. No.: 10/587,372

(22) PCT Filed: Jan. 27, 2005

(86) PCT No.: PCT/ES2005/070010
§ 371 (c)(1),
(2), (4) Date: Jun. 12, 2008

(87) PCT Pub. No.: WO2005/075649
PCT Pub. Date: Aug. 18, 2005

(65) Prior Publication Data
US 2009/0288219 A1    Nov. 19, 2009

(30) Foreign Application Priority Data
Feb. 5, 2004    (ES) .................................. 200400257

(51) Int. Cl.
*A01H 5/00*    (2006.01)
*C12N 15/82*   (2006.01)
*C12N 15/00*   (2006.01)
*C12N 15/10*   (2006.01)

(52) U.S. Cl. ..................... 800/278; 800/295; 435/320.1; 435/468; 536/23.1; 536/23.6

(58) Field of Classification Search .......... None
See application file for complete search history.

(56) References Cited

U.S. PATENT DOCUMENTS
2003/0135870 A1 * 7/2003 Cheikh et al. .................. 800/8

FOREIGN PATENT DOCUMENTS
| WO | 94/28146 | 12/1994 |
| WO | 98/03637 | 1/1998 |
| WO | 99/10511 | 3/1999 |
| WO | 02/45485 | 6/2002 |
| WO | 02/067662 | 9/2002 |

OTHER PUBLICATIONS

Zrenner et al 1995 The Plant Journal 7:97-107.*
Baroja-Fernandez et al 2003 Plant Cell Physiology 44:500-509, provided by Applicant.*
E. Baroja-Fernández, et al; "Sucrose Synthase Catalyzes the de novo Production of ADPglucose Linked to Starch Biosynthesis in Heterotrophic Tissues of Plants"; *Plant Cell Physiol* (2003) 44(5) pp. 500-509.
R. Zrenner, et al; Evidence of the crucial role of sucrose synthase for sink strength using transgenic potato plants (*Solanum tuberosum* L.); *The Plant Journal* (1995); 7(1) pp. 97-107.
J. Pozueta-Romero, et al; "ADPG formation by the ADP-specific cleavage of sucrose-reassessment of sucrose synthase"; *Federation of European Biochemical Societies* (1991) ADONIS 001457939101000L; vol. 291, No. 2; pp. 233-237.
P.S. Chourey et al; "Genetic evidence that the two isozymes of sucrose synthase present in developing maize endosperm are critical, one for cell wall integrity and the other for starch biosynthesis"; *Mol Gen Genet* (1998) 259; pp. 88-96.
M. Salanoubat et al; Molecular cloning and sequencing of sucrose synthase cDNA from potato (*Solanum tuberosum* L.): preliminary characterization of sucrose synthase mRNA distribution; *Gene* (1987) 60 pp. 47-56.
T. Nakai, et al; "Expression and Characterization of Sucrose Synthase from Mung Bean Seedlings in *Escherichia coli*"; *Biosci Biotech, Biochem* (1997) 61 (9), pp. 1500-1503.
T. Nakai, et al; "An Increase in Apparent Affinity for Sucrose of Mung Bean Sucrose Synthase Is Caused by In Vitro Phosphorylation or Directed Mutagenesis if Ser"; *Plant Cell Physiol* (1998) 39(12); pp. 1337-1341.

* cited by examiner

*Primary Examiner* — Brent T Page
(74) *Attorney, Agent, or Firm* — Ladas & Parry LLP

(57) ABSTRACT

An isolated sucrose synthase peptide. Also, a method of preparing ADPglucose by incubating the isolated sucrose synthase peptide with ADP in suitable conditions and then isolating and purifying the ADPG produced. Also, an assay kit for the spectrophotometric, fluorimetric or amperometric determination of sucrose, which kit includes the isolated sucrose synthase peptide. Also, a method of producing a transgenic plant that overexpresses sucrose synthase by inserting a genetic construct containing a DNA fragment that encodes the sucrose synthase peptide into a vector and transferring to a plant genome, and a transgenic plant obtained thereby.

18 Claims, 22 Drawing Sheets

Figure 1:
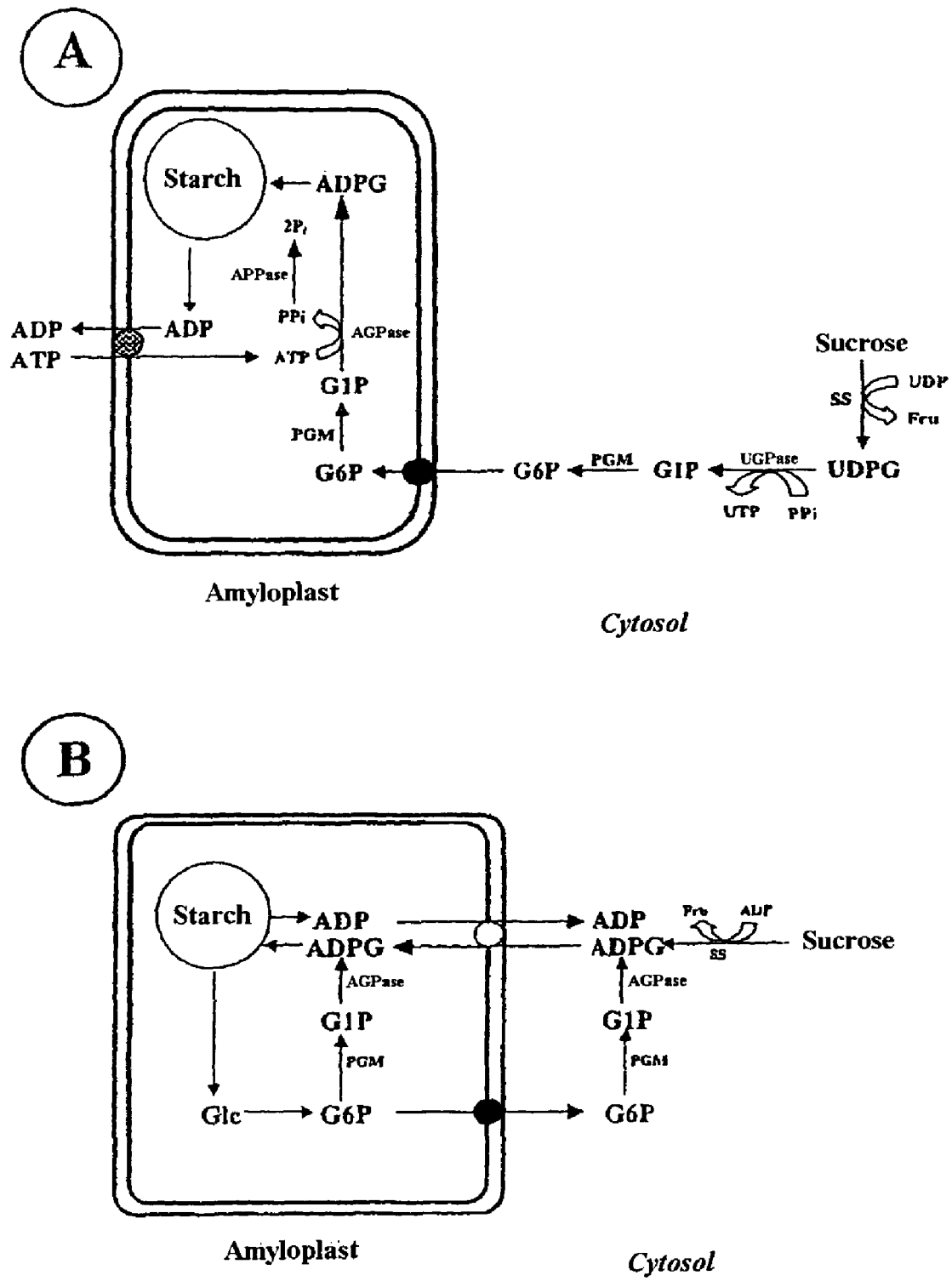

```
                         SEQUENCE LISTING

<160> NUMBER OF SEQ ID NOS: 12

<210> SEQ ID NO 1
<211> LENGTH: 25
<212> TYPE: DNA
<213> ORGANISM: Solanum tuberosum
<220> FEATURE:
<223> OTHER INFORMATION: Promoter of the 5' region of SS4

<400> SEQUENCE: 1
ctgccatggc tgaacgtgtt ttgac                                           25

<210> SEQ ID NO 2
<211> LENGTH: 27
<212> TYPE: DNA
<213> ORGANISM: Solanum tuberosum
<220> FEATURE:
<223> OTHER INFORMATION: Promoter of the 3' region of SS4

<400> SEQUENCE: 2
cttcattcac tcagcagcca atggaac                                         27

<210> SEQ ID NO 3
<211> LENGTH: 2418
<212> TYPE: DNA
<213> ORGANISM: Solanum tuberosum
<220> FEATURE:
<223> OTHER INFORMATION: SSX

<400> SEQUENCE: 3
atggctgaac gtgttttgac tcgtgttcat agccttcgtg aacgtgttga tgcaacttta     60
gctgctcacc gcaatgagat actgctgttt ctttcaagga tcgaaagcca cggaaaaggg    120
atattgaaac ctcatgagct tttggctgag ttcgatgcaa ttcgccaaga tgacaaaaac    180
aaactgaacg aacatgcatt cgaagaactc ctgaaatcca ctcaggaagc gattgttctg    240
cccccttggg ttgcacttgc tattcgtttg aggcctggtg tctgggaata catccgtgtg    300
aacgtcaatg cactagttgt cgaggagctg tccgtccctg agtatttgca attcaaggaa    360
gaacttgtcg acggagcctc gaatggaaat tttgttctcg agttggattt cgagcctttc    420
actgcatcct ttcctaaacc aaccctcacc aaatctattg gaatggagt  tgaattcctc    480 aataggcacc tctctgccaa aatgttccat gacaaggaaa gcatgacccc gcttctcgaa    540
tttcttcgcg ctcaccatta taagggcaag acaatgatgc tgaatgatag gatacagaat    600
tcgaatactc ttcaaaatgt cctaaggaag gcagaggaat acctcattat gctttcccca    660
```

-continued

```
gatactccat atttcgaatt cgagcacaag ttccaagaaa tcggattgga gaagggatgg      720
ggggacacgg cggagcgtgt gctagagatg gtatgcatgc ttcttgatct ccttgaggct      780
cctgactcat gtactcttga gaagttcttg gggagaattc ctatggtttt caatgtggtt      840
atcctttccc ctcatggata ttttgcccaa gaaaatgtct tgggttatcc cgacaccggt      900
ggccaggttg tctacattct agatcaagtt cccgccttgg agcgtgaaat gcttaagcgc      960
ataaaggagc aaggacttga tatcatcccc cgtattctta ttgttactcg tctgctgccc     1020
gatgcagttg aaccacttg tggtcagagg attgagaagg tgtatggagc agaacactca      1080
catattctta gggtcccttt taggactgag aagggcattg ttcgcaaatg gatctctcgc     1140
tttgaagtgt ggccatacat ggagacattc attgaggatg ttgcaaaaga atttctgca      1200
gaacrgcagg ccaagccaga tttgataatt ggaaactaca gtgagggcaa tcttgctgct     1260
tctttgctag ctcacaagtt aggcgtaact cagtgcacsa ttgcccacgc gttggagaaa     1320
acgaagtatc ctgattccga catttactgg aaaaagtttg atgaaaaata ccatttctcg     1380
tcccagttta ccgctgatct cattgcaatg aatcacactg atttcatcat caccagcacc     1440
ttccaggaga ragcaggaag caaggacact gtaggacaat atgagagcca tatggcattc     1500
acaatgcctg gattgtacag agttgttcac ggcattaatg tgttcgaccc caaattcaac     1560
attgtctcac ctggagctga tattaatctc tacttctcgt actccgaaac ggagaagaga     1620
cttacagcat ttcaccctga aattgatgag ctgctgtata gtgatgttga aatgacgag      1680
catctgtgtg tgctcaagga caggactaaa ccaattttat tcacaatggc aaggttggat     1740
cgtgtgaaga atttaactgg acttgttgag tggtacgcca agaatccacg actaagggga     1800
ttggttaacc tggttgtagt tggcggagat cgaaggaagg aatccaaaga tttggaagag     1860
caggcagaga tgaagaagat gtatgagcta attgagactc ataatttgaa tggccaattc     1920
agatggattt cttcccagat gaaccgagtg aggaatggtg agctctaccg atacattgct     1980
gacactaagg gagctttcgt tcagcctgca ttctacgagg cctttggtct gactgttgtc     2040
gaagcaacga crtgtggttt gcctacattt gcaactaatc acggtggtcc agctgagatc     2100
atcgttcatg gaaagtccgg cttccacatt gatccatatc acggtgagca agctgctgat     2160
ctgctagctg atttctttga gaaatgcaag aaagagcctt cacattggga aaccatttcg     2220
acgggtggcc tgaagcgcat ccaagagaag tacacttggc aaatctactc cgaaaggcta     2280
ttgacactgg ctgctgttta tgggrtctgg aaacatgttt ctaaacttga tcgtctagaa     2340
acccgrcgct atcttgasat gttttatgct ctcaagtacc gtaagatggc rgaagctgtt     2400
ccattggcrg ctgagtga                                                   2418
```

```
<210> SEQ ID NO 4
<211> LENGTH: 841
<212> TYPE: PRT
<213> ORGANISM: Solanum tuberosum
<220> FEATURE:
<223> OTHER INFORMATION: SSX fused with a histidine-rich amino acid tail
      deducted after expression of SSX in the PET-28a(+) expression
      plasmid

<400> SEQUENCE: 4

Met Gly Ser Ser His His His His His His Ser Ser Gly Leu Val Pro
1               5                   10                  15

Arg Gly Ser His Met Ala Ser Met Thr Gly Gly Gln Gln Met Gly Arg
            20                  25                  30

Gly Ser Glu Phe Met Ala Glu Arg Val Leu Thr Arg Val His Ser Leu
        35                  40                  45
```

```
Arg Glu Arg Val Asp Ala Thr Leu Ala Ala His Arg Asn Glu Ile Leu
     50                  55                  60

Leu Phe Leu Ser Arg Ile Glu Ser His Gly Lys Gly Ile Leu Lys Pro
 65                  70                  75                  80

His Glu Leu Leu Ala Glu Phe Asp Ala Ile Arg Gln Asp Asp Lys Asn
                 85                  90                  95

Lys Leu Asn Glu His Ala Phe Glu Glu Leu Leu Lys Ser Thr Gln Glu
                100                 105                 110

Ala Ile Val Leu Pro Pro Trp Val Ala Leu Ala Ile Arg Leu Arg Pro
                115                 120                 125

Gly Val Trp Glu Tyr Ile Arg Val Asn Val Asn Ala Leu Val Val Glu
         130                 135                 140

Glu Leu Ser Val Pro Glu Tyr Leu Gln Phe Lys Glu Glu Leu Val Asp
145                 150                 155                 160

Gly Ala Ser Asn Gly Asn Phe Val Leu Glu Leu Asp Phe Glu Pro Phe
                165                 170                 175

Thr Ala Ser Phe Pro Lys Pro Thr Leu Thr Lys Ser Ile Gly Asn Gly
                180                 185                 190

Val Glu Phe Leu Asn Arg His Leu Ser Ala Lys Met Phe His Asp Lys
         195                 200                 205

Glu Ser Met Thr Pro Leu Leu Glu Phe Leu Arg Ala His His Tyr Lys
210                 215                 220

Gly Lys Thr Met Met Leu Asn Asp Arg Ile Gln Asn Ser Asn Thr Leu
225                 230                 235                 240

Gln Asn Val Leu Arg Lys Ala Glu Glu Tyr Leu Ile Met Leu Ser Pro
                245                 250                 255

Asp Thr Pro Tyr Phe Glu Phe Glu His Lys Phe Gln Glu Ile Gly Leu
                260                 265                 270

Glu Lys Gly Trp Gly Asp Thr Ala Glu Arg Val Leu Glu Met Val Cys
         275                 280                 285

Met Leu Leu Asp Leu Leu Glu Ala Pro Asp Ser Cys Thr Leu Glu Lys
290                 295                 300

Phe Leu Gly Arg Ile Pro Met Val Phe Asn Val Val Ile Leu Ser Pro
305                 310                 315                 320

His Gly Tyr Phe Ala Gln Glu Asn Val Leu Gly Tyr Pro Asp Thr Gly
                325                 330                 335

Gly Gln Val Val Tyr Ile Leu Asp Gln Val Pro Ala Leu Glu Arg Glu
                340                 345                 350

Met Leu Lys Arg Ile Lys Glu Gln Gly Leu Asp Ile Ile Pro Arg Ile
                355                 360                 365

Leu Ile Val Thr Arg Leu Leu Pro Asp Ala Val Gly Thr Thr Cys Gly
         370                 375                 380

Gln Arg Ile Glu Lys Val Tyr Gly Ala Glu His Ser His Ile Leu Arg
385                 390                 395                 400

Val Pro Phe Arg Thr Glu Lys Gly Ile Val Arg Lys Trp Ile Ser Arg
                405                 410                 415

Phe Glu Val Trp Pro Tyr Met Glu Thr Phe Ile Glu Asp Val Ala Lys
                420                 425                 430

Glu Ile Ser Ala Glu Leu Gln Ala Lys Pro Asp Leu Ile Ile Gly Asn
                435                 440                 445

Tyr Ser Glu Gly Asn Leu Ala Ala Ser Leu Leu Ala His Lys Leu Gly
450                 455                 460

Val Thr Gln Cys Thr Ile Ala His Ala Leu Glu Lys Thr Lys Tyr Pro
```

```
                    465                 470                 475                 480
Asp Ser Asp Ile Tyr Trp Lys Lys Phe Asp Glu Lys Tyr His Phe Ser
                        485                 490                 495

Ser Gln Phe Thr Ala Asp Leu Ile Ala Met Asn His Thr Asp Phe Ile
                500                 505                 510

Ile Thr Ser Thr Phe Gln Glu Ile Ala Gly Ser Lys Asp Thr Val Gly
                515                 520                 525

Gln Tyr Glu Ser His Met Ala Phe Thr Met Pro Gly Leu Tyr Arg Val
            530                 535                 540

Val His Gly Ile Asn Val Phe Asp Pro Lys Phe Asn Ile Val Ser Pro
545                 550                 555                 560

Gly Ala Asp Ile Asn Leu Tyr Phe Ser Tyr Ser Glu Thr Glu Lys Arg
                    565                 570                 575

Leu Thr Ala Phe His Pro Glu Ile Asp Glu Leu Leu Tyr Ser Asp Val
                580                 585                 590

Glu Asn Asp Glu His Leu Cys Val Leu Lys Asp Arg Thr Lys Pro Ile
            595                 600                 605

Leu Phe Thr Met Ala Arg Leu Asp Arg Val Lys Asn Leu Thr Gly Leu
610                 615                 620

Val Glu Trp Tyr Ala Lys Asn Pro Arg Leu Arg Gly Leu Val Asn Leu
625                 630                 635                 640

Val Val Val Gly Gly Asp Arg Arg Lys Glu Ser Lys Asp Leu Glu Glu
                    645                 650                 655

Gln Ala Glu Met Lys Lys Met Tyr Glu Leu Ile Glu Thr His Asn Leu
                660                 665                 670

Asn Gly Gln Phe Arg Trp Ile Ser Ser Gln Met Asn Arg Val Arg Asn
            675                 680                 685

Gly Glu Leu Tyr Arg Tyr Ile Ala Asp Thr Lys Gly Ala Phe Val Gln
        690                 695                 700

Pro Ala Phe Tyr Glu Ala Phe Gly Leu Thr Val Val Glu Ala Met Thr
705                 710                 715                 720

Cys Gly Leu Pro Thr Phe Ala Thr Asn His Gly Gly Pro Ala Glu Ile
                    725                 730                 735

Ile Val His Gly Lys Ser Gly Phe His Ile Asp Pro Tyr His Gly Glu
                740                 745                 750

Gln Ala Ala Asp Leu Leu Ala Asp Phe Phe Glu Lys Cys Lys Lys Glu
            755                 760                 765

Pro Ser His Trp Glu Thr Ile Ser Thr Gly Gly Leu Lys Arg Ile Gln
        770                 775                 780

Glu Lys Tyr Thr Trp Gln Ile Tyr Ser Glu Arg Leu Leu Thr Leu Ala
785                 790                 795                 800

Ala Val Tyr Gly Phe Trp Lys His Val Ser Lys Leu Asp Arg Leu Glu
                    805                 810                 815

Ile Arg Arg Tyr Leu Glu Met Phe Tyr Ala Leu Lys Tyr Arg Lys Met
                820                 825                 830

Ala Glu Ala Val Pro Leu Ala Ala Glu
            835                 840

<210> SEQ ID NO 5
<211> LENGTH: 41
<212> TYPE: DNA
<213> ORGANISM: Solanum tuberosum
<220> FEATURE:
<223> OTHER INFORMATION: "Forward" promoter required for the point
      mutagenesis of SSX
```

-continued

```
<400> SEQUENCE: 5
cgaacatgca ttcgaagaac ccctgaaatc cactcaggaa g                    41

<210> SEQ ID NO 6
<211> LENGTH: 41
<212> TYPE: DNA
<213> ORGANISM: Solanum tuberosum
<220> FEATURE:
<223> OTHER INFORMATION: "Reverse" promoter required for the point
      mutagenesis of SSX

<400> SEQUENCE: 6
cttcctgagt ggatttcagg ggttcttcga atgcatgttc g                    41

<210> SEQ ID NO 7
<211> LENGTH: 42
<212> TYPE: DNA
<213> ORGANISM: Solanum tuberosum
<220> FEATURE:
<223> OTHER INFORMATION: "Forward" promoter required for point
      mutagenesis of SSX

<400> SEQUENCE: 7
cggagaagag acttacagca tctcaccctg aaattgatga gc                   42

<210> SEQ ID NO 8
<211> LENGTH: 42
<212> TYPE: DNA
<213> ORGANISM: Solanum tuberosum
<220> FEATURE:
<223> OTHER INFORMATION: "Reverse" promoter required for the point
      mutagenesis of SSX

<400> SEQUENCE: 8
gctcatcaat ttcagggtga gatgctgtaa gtctcttctc cg                   42

<210> SEQ ID NO 9
<211> LENGTH: 76
<212> TYPE: DNA
<213> ORGANISM: Solanum tuberosum
<220> FEATURE:
<223> OTHER INFORMATION: "Forward" promoter required for point
      mutagenesis of SSX and production of SS5

<400> SEQUENCE: 9
gatttctttg agaaatgcaa gagagagcct tcacattggg aaaccatttc gacggatggc    60
ctgaagcgca tccaag                                                    76

<210> SEQ ID NO 10
<211> LENGTH: 76
<212> TYPE: DNA
<213> ORGANISM: Solanum tuberosum
<220> FEATURE:
<223> OTHER INFORMATION: "Reverse" promoter required for point
      mutagenesis of SSX and production of SS5

<400> SEQUENCE: 10
cttggatgcg cttctggcca tccgtcgaaa tggtttccca atgtgaaggc tctctcttgc    60
atttctcaaa gaaatc                                                    76

<210> SEQ ID NO 11
<211> LENGTH: 2424
<212> TYPE: DNA
<213> ORGANISM: Solanum tuberosum
<220> FEATURE:
<223> OTHER INFORMATION: SS5
```

<400> SEQUENCE: 11

```
atggctgaac gtgttctgac tcgtgttcat agccttcgtg aacgtgtrga tgcaactcta        60
gctgcccacc gcaatgagat actgctgttt ctttcaagga tcgaaagcca cggaaaaggg       120
atattgaaac ctcacgagct tttggctgag ttcgatgcaa ttcgccaaga tgacaaaaac       180
aaactgaacg aacatgcatt cgaagaaccc ctgaaatcca ctcaggaagc gattgttctg       240
cccccttggg ttgcacttgc tattcgtttg aggcctggtg tctgggaata catccgtgtg       300
aacgtcaatg cactagttgt cgaggagctg tccgtccctg agtatttgca attcaaggaa       360
gaacttgtcg acggagcctc gaatggaaat ttcgttctcg agttggattt cgagcctttc       420
actgcatcct ttcctaaacc aaccctcacc aaatctattg aaatggagt tgaattcctc        480
aataggcacc tctctgccaa atgttccat gacaaggaaa gcatgacccc gcttctcgaa        540
tttcttcgcg ctcaccatta agggcaag acaatgatgc tgaatgatag atacagaat         600
tcgaatactc ttcaaaatgt cctaaggaag gcagaggaat acctcactat gctttcccca      660
gatactccat atttcgaatt cgagcacaag ttccaagaaa tcggattgga aagggatgg       720
ggggacacgc ggagcgtgt gctagagatg gtatgcatgc ttcttgatct ccttgaggct       780
cctgactcat gtactcttga aagttcttg gggagaattc ctatggtttt caatgtggtt      840
atcctttccc ctcatggata ttttgcccaa gaaaatgtct tgggttatcc cgacaccggt      900
ggccaggttg tctacatttt agatcaagtt cccgccttgg agcgtgaaat gcttaagcgc      960
ataaaggagc aaggacttga tatcatcccc cgtattctta ttgttactcg tctgctgccc      1020
gatgcagttg aaccacttg tggtcagagg attgagaagg tgtatggagc agaacactca       1080
catattctta gggtcccttt taggactgag aagggcattg ttcgcaaatg gatctctcgc      1140
tttgaagtgt ggccatacat ggagacattc attgaggatg ttgcaaaaga aacttctgca      1200
gaactgcagg ccaagccaga tttgataatt ggaaactaca gtgagggcaa tcttgctgct      1260
tcttggctag ctcacaagtt aggcgtaact cagtgcacca ttgcccacgc gttggagaaa      1320
acgaagtatc ctgattccga catttactgg aaaaagtttg atgaaaaata ccatttctcg      1380
tcccagtttta ccgctgatct cattgcaatg aatcacactg atttcatcat caccaycacc    1440
ttccaggaga tagcaggaag caaggacact gtgggacaat atgagagcca tatggcattc      1500
acaatgcctg gattgtacag agttgttcat ggcattaatg tgttcgaccc caaattcaac     1560
attgtctcac ctggagctga tattaacctc tacttctcgt actccgaaac ggaaaagaga      1620
cttacagcat ctcaccctga aattgatgag ctgctgtata gtgacgttga aatgacgaa      1680
catctgtgtg tgctcaagga taggactaaa ccaattttat tcacaatggc aaggttggat     1740
cgtgtgaaga atttaactgg acttgttgag tggtacgcca agaatccacg actaagggga     1800
ttggttaacc tggttgtagt tggcggagat cgaaggaagg aatccaaaga tttggaagag     1860
caggcagaga tgaagaagat gtatgagcta atagagactc ataatttgaa tggccaattc     1920
agatggattt cttcccagat gaaccgagtg aygaatggtg ayctctaccg atacattgct     1980
gacactaagg gagctttcgt tcagcctgca ttctacgagg cttttggtct gactgttgtc     2040
gaaacaatga cttgtggttt gcctacattt gcaactaatc acggtggtcc agctgagatc     2100
atcgttcatg gaaagtccgg cttccacatt gatccatatc acggtgagca agctgctgat     2160
ctgctagctg atttctttga gaatgcaaag agagagcctt cacattggga aaccatttcg     2220
acggatggcc tgaagcgcat ccaagagaag tacacctggc aaatctactc cgaaaggcta     2280
ttgacactgg ctgctgttta tgggttctgg aaacatgttt ctaagcttga tcgtctagaa     2340
```

```
atccgtcgct atcttgaaat gttttatgct ctcaagtacc gtaagatggc tgaagctgtt    2400
ccattggctg ctgagtgaat gaag                                            2424
```

<210> SEQ ID NO 12
<211> LENGTH: 841
<212> TYPE: PRT
<213> ORGANISM: Solanum tuberosum
<220> FEATURE:
<223> OTHER INFORMATION: SS5 fused with a histidine-rich amino acid
      sequence

<400> SEQUENCE: 12

```
Met Gly Ser Ser His His His His His Ser Ser Gly Leu Val Pro
1               5                   10                  15

Arg Gly Ser His Met Ala Ser Met Thr Gly Gly Gln Gln Met Gly Arg
            20                  25                  30

Gly Ser Glu Phe Met Ala Glu Arg Val Leu Thr Arg Val His Ser Leu
        35                  40                  45

Arg Glu Arg Val Asp Ala Thr Leu Ala Ala His Arg Asn Glu Ile Leu
    50                  55                  60

Leu Phe Leu Ser Arg Ile Glu Ser His Gly Lys Gly Ile Leu Lys Pro
65                  70                  75                  80

His Glu Leu Leu Ala Glu Phe Asp Ala Ile Arg Gln Asp Asp Lys Asn
                85                  90                  95

Lys Leu Asn Glu His Ala Phe Glu Glu Pro Leu Lys Ser Thr Gln Glu
            100                 105                 110

Ala Ile Val Leu Pro Pro Trp Val Ala Leu Ala Ile Arg Leu Arg Pro
        115                 120                 125

Gly Val Trp Glu Tyr Ile Arg Val Asn Val Asn Ala Leu Val Val Glu
    130                 135                 140

Glu Leu Ser Val Pro Glu Tyr Leu Gln Phe Lys Glu Glu Leu Val Asp
145                 150                 155                 160

Gly Ala Ser Asn Gly Asn Phe Val Leu Glu Leu Asp Phe Glu Pro Phe
                165                 170                 175

Thr Ala Ser Phe Pro Lys Pro Thr Leu Thr Lys Ser Ile Gly Asn Gly
            180                 185                 190

Val Glu Phe Leu Asn Arg His Leu Ser Ala Lys Met Phe His Asp Lys
        195                 200                 205

Glu Ser Met Thr Pro Leu Leu Glu Phe Leu Arg Ala His His Tyr Lys
    210                 215                 220

Gly Lys Thr Met Met Leu Asn Asp Arg Ile Gln Asn Ser Asn Thr Leu
225                 230                 235                 240

Gln Asn Val Leu Arg Lys Ala Glu Glu Tyr Leu Ile Met Leu Ser Pro
                245                 250                 255

Asp Thr Pro Tyr Phe Glu Phe Glu His Lys Phe Gln Glu Ile Gly Leu
            260                 265                 270

Glu Lys Gly Trp Gly Asp Thr Ala Glu Arg Val Leu Glu Met Val Cys
        275                 280                 285

Met Leu Leu Asp Leu Leu Glu Ala Pro Asp Ser Cys Thr Leu Glu Lys
    290                 295                 300
```

-continued

```
Phe Leu Gly Arg Ile Pro Met Val Phe Asn Val Val Ile Leu Ser Pro
305                 310                 315                 320

His Gly Tyr Phe Ala Gln Glu Asn Val Leu Gly Tyr Pro Asp Thr Gly
            325                 330                 335

Gly Gln Val Val Tyr Ile Leu Asp Gln Val Pro Ala Leu Glu Arg Glu
        340                 345                 350

Met Leu Lys Arg Ile Lys Glu Gln Gly Leu Asp Ile Ile Pro Arg Ile
    355                 360                 365

Leu Ile Val Thr Arg Leu Leu Pro Asp Ala Val Gly Thr Thr Cys Gly
370                 375                 380

Gln Arg Ile Glu Lys Val Tyr Gly Ala Glu His Ser His Ile Leu Arg
385                 390                 395                 400

Val Pro Phe Arg Thr Glu Lys Gly Ile Val Arg Lys Trp Ile Ser Arg
            405                 410                 415

Phe Glu Val Trp Pro Tyr Met Glu Thr Phe Ile Glu Asp Val Ala Lys
        420                 425                 430

Glu Ile Ser Ala Glu Leu Gln Ala Lys Pro Asp Leu Ile Ile Gly Asn
    435                 440                 445

Tyr Ser Glu Gly Asn Leu Ala Ala Ser Leu Leu Ala His Lys Leu Gly
450                 455                 460

Val Thr Gln Cys Thr Ile Ala His Ala Leu Glu Lys Thr Lys Tyr Pro
465                 470                 475                 480

Asp Ser Asp Ile Tyr Trp Lys Lys Phe Asp Glu Lys Tyr His Phe Ser
            485                 490                 495

Ser Gln Phe Thr Ala Asp Leu Ile Ala Met Asn His Thr Asp Phe Ile
        500                 505                 510

Ile Thr Ser Thr Phe Gln Glu Ile Ala Gly Ser Lys Asp Thr Val Gly
    515                 520                 525

Gln Tyr Glu Ser His Met Ala Phe Thr Met Pro Gly Leu Tyr Arg Val
530                 535                 540

Val His Gly Ile Asn Val Phe Asp Pro Lys Phe Asn Ile Val Ser Pro
545                 550                 555                 560

Gly Ala Asp Ile Asn Leu Tyr Phe Ser Tyr Ser Glu Thr Glu Lys Arg
            565                 570                 575

Leu Thr Ala Ser His Pro Glu Ile Asp Glu Leu Leu Tyr Ser Asp Val
        580                 585                 590

Glu Asn Asp Glu His Leu Cys Val Leu Lys Asp Arg Thr Lys Pro Ile
    595                 600                 605

Leu Phe Thr Met Ala Arg Leu Asp Arg Val Lys Asn Leu Thr Gly Leu
610                 615                 620

Val Glu Trp Tyr Ala Lys Asn Pro Arg Leu Arg Gly Leu Val Asn Leu
625                 630                 635                 640

Val Val Val Gly Gly Asp Arg Arg Lys Glu Ser Lys Asp Leu Glu Glu
            645                 650                 655

Gln Ala Glu Met Lys Lys Met Tyr Glu Leu Ile Glu Thr His Asn Leu
        660                 665                 670

Asn Gly Gln Phe Arg Trp Ile Ser Ser Gln Met Asn Arg Val Arg Asn
    675                 680                 685

Gly Glu Leu Tyr Arg Tyr Ile Ala Asp Thr Lys Gly Ala Phe Val Gln
690                 695                 700

Pro Ala Phe Tyr Glu Ala Phe Gly Leu Thr Val Val Glu Ala Met Thr
705                 710                 715                 720

Cys Gly Leu Pro Thr Phe Ala Thr Asn His Gly Gly Pro Ala Glu Ile
            725                 730                 735
```

```
Ile Val His Gly Lys Ser Gly Phe His Ile Asp Pro Tyr His Gly Glu
            740                 745                 750

Gln Ala Ala Asp Leu Leu Ala Asp Phe Phe Glu Lys Cys Lys Arg Glu
            755                 760                 765

Pro Ser His Trp Glu Thr Ile Ser Thr Asp Gly Leu Lys Arg Ile Gln
            770                 775                 780

Glu Lys Tyr Thr Trp Gln Ile Tyr Ser Glu Arg Leu Leu Thr Leu Ala
785                 790                 795                 800

Ala Val Tyr Gly Phe Trp Lys His Val Ser Lys Leu Asp Arg Leu Glu
                805                 810                 815

Ile Arg Arg Tyr Leu Glu Met Phe Tyr Ala Leu Lys Tyr Arg Lys Met
            820                 825                 830

Ala Glu Ala Val Pro Leu Ala Ala Glu
            835                 840
```

METHOD OF PRODUCTION OF RECOMBINANT SUCROSE SYNTHASE, USE THEREOF IN THE MANUFACTURE OF KITS FOR DETERMINATION OF SUCROSE, PRODUCTION OF ADPGLUCOSE AND PRODUCTION OF TRANSGENIC PLANTS WHOSE LEAVES AND STORAGE ORGANS ACCUMULATE HIGH CONTENTS OF ADPGLUCOSE AND STARCH

AREA OF INDUSTRY TO WHICH THE INVENTION RELATES

The invention relates to optimization of the production of recombinant sucrose synthase (SS) in soluble, active form employing an appropriate strain of *Escherichia coli*, the use of SS for making kits for determination of sucrose, design of optimized forms of SS for the synthesis of ADPglucose (ADPG), and the production of transgenic plants whose leaves and storage tissues accumulate high levels of ADPG and amylose-enriched starch as a result of overproduction of cytosolic ADPG in plants which overexpress SS.

PRIOR ART

Starch is the main storage form of carbohydrates in plants. It accumulates in large amounts in organs such as seeds (wheat, barley, maize, pea, etc.) and tubers (potato and yam among others) and is a fundamental constituent of the human diet. Furthermore, starch is widely used in the paper, cosmetic, pharmaceutical and food industries, and is also used as an essential component for the manufacture of biodegradable plastics and environment-friendly paints. Since it is made up of covalently bound glucose molecules, investigation of the processes involved in the synthesis of this polysaccharide is a top priority in various areas of industrial production.

ADPG is the universal precursor of starch biosynthesis in plants, both in heterotrophic organs (FIG. 1A) and in leaves (FIG. 2A), and it is widely assumed that its production is controlled exclusively by the enzyme ADPG pyrophosphorylase (AGPase) or ADPG synthase (EC 2.7.7.27) (Okita, T. W. (1992) Is there an alternative pathway for starch synthesis? Plant Physiol. 100, 560-56; Müller-Röber, B., Sonnewald, U. Willmitzer, L. (1992) Inhibition of the ADPglucose pyrophosphorylase in transgenic potatoes leads to sugar-storing tubers and influences tuber formation and expression of tuber storage protein genes. EMBO J. 11, 1229-1238; Stark, D. M., Timmerman, K. P., Barry, G. F., Preiss, J., Kishore, G. M. (1992) Regulation of the amount of starch in plant tissues by ADPglucose pyrophosphorylase. Science 258, 287-282; Neuhaus, E. H., Häusler, R. E., Sonnewald, U. (2005) No time to shift the paradigm on the metabolic pathway to transitory starch in leaves. Trends Plant Sci. at press). The various applications of the starch produced in a plant are based mainly on the ratio of amylose and amylopectin, which determines the structure of the starch grain, as well as its viscosity in aqueous suspensions. This ratio of amylose and amylopectin depends on, among other things, the concentration of ADPG in the plant cell (Clarke, B. R., Denyer, K., Jenner, C. F., Smith, A. M. (1999) The relationship between the rate of starch synthesis, the adenosine 5'-diphosphoglucose concentration and the amylose content of starch in developing pea embryos. Planta 209, 324-329).

SS (EC 2.4.1.13, SS) (UDP-glucose:D-fructose-2-glucosyl transferase) is a reversible enzyme that catalyses the production of UDPG and fructose from sucrose and UDP. Although, as shown in FIG. 1A, SS has classically been regarded as having the role of producing UDPG, metabolic processing of which eventually gives rise to the production of starch in heterotrophic tissues such as endosperm and tubers (Zrenner, R., Salanoubat, M., Willmitzer, L., Sonnewald, U. (1995) Evidence for the crucial role of sucrose synthase for sink strength using transgenic potato plants. Plant J. 7, 97-107; Baroja-Fernández, E., Muñoz, F. J., Saikusa, T., Rodríguez-López, M., Akazawa, T., Pozueta-Romero, J. (2003) Sucrose synthase catalyzes the de novo production of ADPglucose linked to starch biosynthesis in heterotrophic tissues of plants. Plant Cell Physiol. 44, 500-509; Pozueta-Romero, J., Muñoz, F. J., Rodríguez-López, M., Baroja-Fernández, E., Akazawa, T. (August 2003) New waves in the starch field. Lett. Plant Cell Physiol. 24-32), there are references to the potential ability of the enzyme to use other nucleotide diphosphates in vitro for the production of the corresponding sugar nucleotides (Murata, T., Sugiyama, T., Minamikawa, T., Akazawa, T. (1966) Enzymic mechanism of starch synthesis in ripening rice grains. Mechanism of the sucrose-starch conversion. Arch. Biochem. Biophys. 113, 34-44; Delmer, D. P. (1972) The purification and properties of sucrose synthase from etiolated *Phaseolus aureus* seedlings. J. Biol. Chem. 247, 3822-3828). Although of questionable physiological relevance (Okita, T. W. (1992) Is there an alternative pathway for starch synthesis? Plant Physiol. 100, 560-56; Müiller-Röber, B., Sonnewald, U. Willmitzer, L. (1992) Inhibition of the ADPglucose pyrophosphorylase in transgenic potatoes leads to sugar-storing tubers and influences tuber formation and expression of tuber storage protein genes. EMBO J. 11, 1229-1238), it has been suggested that SS is capable of producing ADPG directly, which can be used for the production of starch both in heterotrophic tissues and in photosynthetic tissues (FIGS. 1B and 2B) (Pozueta-Romero, J., Perata, P., Akazawa, T. (1999) Sucrose-starch conversion in heterotrophic tissues of plants. Crit. Rev. Plant Sci. 18, 489-525; Baroja-Fernández, E., Muñoz, F. J., Akazawa, T., Pozueta-Rñomero, J. (2001) Reappraisal of the currently prevailing model of starch biosynthesis in photosynthetic tissues: a proposal involving the cytosolic production of ADPglucose by sucrose synthase and occurrence of cyclic turnover of starch in the chloroplast. Plant Cell Physiol. 42, 1311-1320; Baroja-Fernández, E., Muñoz, F. J., Saikusa, T., Rodríguez-López, M., Akazawa, T., Pozueta-Romero, J. (2003) Sucrose synthase catalyzes the de novo production of ADPglucose linked to starch biosynthesis in heterotrophic tissues of plants. Plant Cell Physiol. 44, 500-509; Baroja-Fernández, E., Muñoz, F. J., Zandueta-Criado, A., Morán-Zorzano, M. T., Viale, A. M., Alonso-Casajús, N., Pozueta-Romero, J. (2004) Most of ADPglucose linked to starch biosynthesis occurs outside the chloroplast in source leaves. Proc. Natl. Acad. Sci. USA 101, 13080-13085). According to this hypothesis (based solely and circumstantially on evidence of the biochemical type), SS is responsible for the synthesis of an important pool of ADPG molecules necessary for the biosynthesis of starch. This hypothesis has not, however, been demonstrated experimentally by genetic engineering or traditional crop improvement techniques, and is not consistent with the countless tests of the genetic and molecular type indicating that AGPase is the only source of ADPG in plants (Okita, T. W. (1992) Is there an alternative pathway for starch synthesis? Plant Physiol. 100, 560-56; Müller-Röber, B., Sonnewald, U. Willmitzer, L. (1992) Inhibition of the ADPglucose pyrophosphorylase in transgenic potatoes leads to sugar-storing tubers and influences tuber formation and expression of tuber storage protein genes. EMBO J. 11, 1229-1238; Neuhaus, E. H., Häusler, R.

E., Sonnewald, U. (2005) No time to shift the paradigm on the metabolic pathway to transitory starch in leaves. Trends Plant Sci. at press).

Sugar nucleotides such as UDPG and ADPG are produced commercially from pyrophosphorylase reactions catalysed by enzymes such as UDPG pyrophosphorylase (UGPase) and AGPase, respectively, based on the use of an expensive substance called glucose-1-phosphate (G1P). An alternative to this practice for production of sugar nucleotides is based on the use of SS, development of which has largely been hampered by the limitations of *Escherichia coli* for expressing and efficiently processing a large number of eukaryotic proteins. This limitation inspired some researchers to produce recombinant SS by making use of biological factories of the eukaryotic type such as yeasts (Zervosen, A., Rṁomer, U., Elling, L. (1998) Application of recombinant sucrose synthase-large scale synthesis of ADP-glucose. J. Mol. Catalysis. B: Enzymatic 5, 25-28; Römer, U., Schrader, H., Günther, N., Nettelstroth, N., Frommer, W. B., Elling, L. (2004) Expression, purification and characterization of recombinant sucrose synthase I from *Solanum tuberosum* L. for carbohydrate engineering. J. Biotechnology 107, 135-149). Alternatively, SS intended for the production of sugar nucleotides has had to be purified by expensive processes of purification of proteins from plant extracts (patent DE4221595 (1993), Purified sucrose synthase enzyme useful for production of nucleotide-activated sugars or oligosaccharides). This SS obtained from plant extracts has the disadvantage that it has a predilection for UDP and very low affinity for ADP (Pressey R (1969) Potato sucrose synthase: purification, properties, and changes in activity associated with maturation. Plant Physiol. 44, 759-764; Nguyen-Quock, B., Krivitzky, M., Huber, S. C., Lecharny, A. (1990) Sucrose synthase in developing maize leaves. Plant Physiol. 94, 516-523; Morell, M., Copeland, L. (1985) Sucrose synthase of soybean nodules. Plant Physiol. 78, 149-154). Production of recombinant SS from cultures of *E. coli* has recently been achieved (Nakai, T., Tonouchi, N., Tsuchida, T., Mori, H., Sakai, F., Hayashi, T. (1997) "Expression and characterization of sucrose synthase from mung bean seedlings in *Escherichia coli*" Biosci. Biotech. Biochem. 61, 1500-1503; Nakai, T., Konishi, T., Zhang, Z-Q., Chollet, R., Tonouchi, N., Tsuchida, T., Yoshinaga, F., Mori, H., Sakai, F., Hayashi, T. (1997) "An increase in apparent affinity for sucrose of mung bean sucrose synthase is caused by in vitro phosphorylation or directed mutagenesis of Ser11" Plant Cell Physiol. 39, 1337-1341; Barratt, D. H. P., Barber, L., Kruger, N. J., Smith, A. M., Wang, T. L., Martin, C. (2001) Multiple, distinct isoforms of sucrose synthase in pea. Plant Physiol. 127, 655-664; Christopher, B., William, B., Robert, H. "Bacterial sucrose synthase compositions and methods of use" Patent WO9803637). However, the production of SS in this prokaryotic system was associated with problems such as (1) the amount of SS produced was very low (30 micrograms/gram of bacteria, Nakai, T., Tonouchi, N., Tsuchida, T., Mori, H., Sakai, F., Hayashi, T. (1997) "Expression and characterization of sucrose synthase from mung bean seedlings in *Escherichia coli*" Biosci. Biotech. Biochem. 61, 1500-1503; Li, C. R., Zhang, X. B., Hew, C. S. (2003) "Cloning, characterization and expression analysis of a sucrose synthase gene from tropical epiphytic orchid *Oncidium goldiana*. Physiol. Plantarum 118, 352-360), (2) the amount of active SS obtained was very low or zero (0.05-1.5 units/mg (Nakai, T., Tonouchi, N., Tsuchida, T., Mori, H., Sakai, F., Hayashi, T. (1997) "Expression and characterization of sucrose synthase from mung bean seedlings in *Escherichia coli*" Biosci. Biotech. Biochem. 61, 1500-1503; Li, C. R., Zhang, X. B., Hew, C. S. (2003) "Cloning, characterization and expression analysis of a sucrose synthase gene from tropical epiphytic orchid *Oncidium goldiana*. Physiol. Plantarum 118, 352-360); 5.6 U/mg (Rṁomer, U., Schrader, H., Günther, N., Nettelstroth, N., Frommer, W. B., Elling, L. (2004) Expression, purification and characterization of recombinant sucrose synthase I from *Solanum tuberosum* L. for carbohydrate engineering. J. Biotechnology 107, 135-149), (3) the recombinant SS had to be purified by conventional methods of purification of proteins such as chromatography, electrophoresis, isoelectric focusing, etc., which, combined, prove expensive and do not guarantee purification of the protein in a homogeneous state and (4) most of the SS is sent to inclusion bodies or is accumulated in the form of inactive aggregates as a result of the inability of the bacterium's machinery to fold the protein correctly (Miroux, B., Walker, J. E. (1996) "Over-production of proteins in *Escherichia coli*: mutant hosts that allow synthesis of some membrane proteins and globular proteins at high levels" J. Mol. Biol. 260, 289-298).

The present invention describes the development of a system based on the use of an appropriate strain of *E. coli* and on the use of a suitable expression vector that permits the large-scale production and fast and easy purification of different variants of recombinant SS in its active form. Some of these variants have greater affinity for ADP than those obtained from plant extracts and can be used both for the production of UDPG and ADPG from inexpensive substances such as sucrose, UDP and ADP.

Chromatographic techniques constitute a powerful tool for determining the sucrose content of complex samples such as plant extracts, sera, urine, fruit juice, wines, fruit and foodstuffs (D'Aoust, M-A., Yelle, S, Nguyen-Quock, B. (1999) Antisense inhibition of tomato fruit sucrose synthase decreases fruit setting and the sucrose unloading capacity of young fruit. Plant Cell 11, 2407-2418; Tang, G-Q., Sturm, A. (1999) Antisense repression of sucrose synthase in carrot affects growth rather than sucrose partitioning. Plant Mol. Biol. 41, 465-479; Frias, J., Price, K. R., Fenwich, G. R., Hedley, C. L., Sorensen, H., Vidal-Valverde, C. (1996) J. Chromatogr. A 719, 213-219). Such techniques require highly specialized technical personnel and involve a large investment in equipment. Unfortunately, alternative methods based on hydrolysis of the sucrose molecule by the action of the enzyme invertase and subsequent spectrophotometric or fluorimetric determination of the molecules of glucose and/or fructose (Sweetlove, L. J., Burrell, M. M., ap Rees, T. (1996) Starch metabolism in tubers of transgenic potato with increased ADPglucose pyrophosphorylase. Biochem. J. 320, 493-498; Stitt, M., Lilley, R. M., Gerhardt, R., Heldt, H. W. (1989) Metabolite levels in specific cells and subcellular compartments of plant leaves. Methods Enzymol. 174, 518-552; Holmes, E. W. (1997) Coupled enzymatic assay for the determination of sucrose. Anal. Biochem. 244, 103-109; Methods of Analysis (1996) Code of Practice for Evaluation of Fruit and Vegetable Juices. Association of the Industry of Juices and Nectars from Fruits and Vegetables of the European Economic Community) are subject to limitations of a technical nature such as subtraction of the measurements corresponding to the endogenous glucose and/or fructose present in the sample. The abundance of glucose and/or fructose in the sample can add background noise that hampers reliable and accurate determination of sucrose. In the vast majority of cases it is necessary to carry out exhaustive controls before issuing a reliable statement on the true sucrose content of a sample (Worrell, A. C., Bruneau, J-M., Summerfelt, K., Boersig, M., Voelker, T. A. (1991) Expression of a maize sucrose phosphate synthase in tomato alters leaf carbohydrate partitioning. Plant Cell 3, 1121-1130). Kits for determination of sucrose based on the use of invertase are available from companies such as Sigma, Biopharm GmbH and Megazyme. Alternatively, an automated method of sucrose determination has been developed, based on determination of the glucose-1-phosphate released by the action of sucrose phosphorylase of bacterial origin (Vinet, B., Panzini, B., Boucher, M., Massicotte, J. (1998) Automated enzymatic assay for the determination of sucrose in serum and urine and its use as a marker of gastric damage. Clin. Chem. 44, 2369-2371). The present invention describes the development of a simple, reliable and inexpensive alternative method for the determination of sucrose in a sample based on the use of SS and coupling enzymes which hydrolyse ADPG or UDPG.

Considerations concerning the factors governing the intracellular levels of ADPG have mainly revolved around regulation of the synthesizing enzyme, AGPase (Preiss, (1988) Biosynthesis of starch and its regulation. The Biochemistry of Plants. Vol. 14, Academic Press, New York, p. 182-249; Pozueta-Rṁomero, J., Perata, P., Akazawa, T. (1999) Sucrose-starch conversion in heterotrophic tissues. Crit. Rev. Plant. Sci. 18, 489-525). In fact, a high proportion of the patents and scientific publications concerning the production of ADPG and the production of plants producing starches of industrial interest revolve around the use of AGPase (Stark, D. M., Timmerman, K. P., Barry, G. F., Preiss, J., Kishore, G. M. (1992) Regulation of the amount of starch in plant tissues by ADPglucose pyrophosphorylase. Science 258, 287-282; Slattery, C. J., Kavakli, H., Okita, T. W. (2000) Engineering starch for increased quantity and quality. Trends Plant Sci. 5, 291-298). However, although they are yet to be confirmed with evidence of the genetic/molecular type, recent scientific studies of a biochemical type indicate that, as shown in FIGS. 1B and 2B, SS might be involved in the direct synthesis of ADPG necessary for the biosynthesis of starch (Baroja-Fernández, E., Muñoz, F. J., Saikusa, T., Rodríguez-López, M., Akazawa, T., Pozueta-Rṁomero, J. (2003) Sucrose synthase catalyzes the de novo production of ADPglucose linked to starch biosynthesis in heterotrophic tissues of plants. Plant Cell Physiol. 44, 500-509). This hypothesis is especially controversial, bearing in mind that (a) SS has never been linked to starch production in leaves, (b) presence of an ADPG translocator is required in the membranes of the plastids, connecting the cytosolic pool of the ADPG produced by SS to the starch synthase present inside the plastid and (c) the involvement of SS as an ADPG producing source is in direct conflict with many tests of the biochemical/genetic/molecular type which appear to show that AGPase is the only source of ADPG (Okita, T. W. (1992) Is there an alternative pathway for starch synthesis? Plant Physiol. 100, 560-56; Möuller-Röbber, B., Sonnewald, U. Willmitzer, L. (1992) Inhibition of the ADPglucose pyrophosphorylase in transgenic potatoes leads to sugar-storing tubers and influences tuber formation and expression of tuber storage protein genes. EMBO J. 11, 1229-1238; Stark, D. M., Timmerman, K. P., Barry, G. F., Preiss, J., Kishore, G. M. (1992) Regulation of the amount of starch in plant tissues by ADPglucose pyrophosphorylase. Science 258, 287-282; Neuhaus, E. H., Häusler, R. E., Sonnewald, U. (2005) No time to shift the paradigm on the metabolic pathway to transitory starch in leaves. Trends Plant Sci. at press). Perhaps for all these reasons, to date plants have never been designed that overexpress SS for the production of high levels of starch. However, the present invention describes, for the first time, the production of transgenic plants that overexpress SS for increasing their production of ADPG and starch. Conversely, we show that plants that are deficient in starch as a result of absence of AGPase possess normal ADPG levels. This all shows that, as shown in FIGS. 1B and 2B, SS is involved in the direct synthesis of the ADPG required for the biosynthesis of starch and is responsible for the synthesis of most of the ADPG accumulated in the plant cell.

Although based on the approach presented in FIG. 1A, according to which SS is involved in the synthesis of UDPG (but not ADPG) in storage tissues, various works have described the production of plants with reduced content of starch as a consequence of decreased activity of SS (Chourey, P. S., Nelson, O. E. (1976) The enzymatic deficiency conditioned by the shrunken-1 mutations in maize. Biochem. Genet. 14, 1041-1055; Zrenner, R., Salanoubat, M., Willmitzer, L., Sonnewald, U. (1995) Evidence for the crucial role of sucrose synthase for sink strength using transgenic potato plants. Plant J. 7, 97-107; Tang, G-Q., Sturm, A. (1999) Antisense repression of sucrose synthase in carrot (*Daucus carota* L.) affects growth rather than sucrose partitioning. Plant Mol. Biol. 41, 465-479). In this sense, there is no experimental evidence that the overexpression of SS could be used for the production of plants with high starch content as a result of the increase in levels of ADPG in accordance with the metabolic schemes shown in FIGS. 1B and 2B. However, based on the ability of SS to produce the precursor molecule of the biosynthesis of cell wall polysaccharides (UDPG), works have been published and patented which describe the production of cotton plants with high fibre content or cereals with high content of celluloses as a result of overexpression of SS (Timothy, H. J., Xiamomu, N., Kanwarpal, S. "Manipulation of sucrose synthase genes to improve stalk and grain quality" Patent WO02067662; Robert, F., Danny, L., Yong-Ling, R. "Modification of sucrose synthase gene expression in plant tissue and uses therefor" Patent WO0245485; Christopher, B., William, B., Robert, H. "Bacterial sucrose synthase compositions and methods of use" Patent WO9803637).

The invention relates firstly to the development and optimization of a method of production of large amounts of recombinant SS that is soluble, can be purified easily and has high specific activity, based on the use of a suitable strain of *E. coli* and on the use of an expression vector that makes it possible to obtain SS with a histidine tail. The invention further relates to the procedure followed for making kits for determination of sucrose based on the use of the enzyme product with SS activity coupled to enzymes that metabolize ADPG or UDPG. It further relates to optimization of the production of sugar nucleotides such as ADPG or UDPG starting from variants of SS specially designed for this purpose. Finally, details are given of the design of transgenic plants with high content of sucrose, ADPG and starch and a high amylose/amylopectin ratio following overexpression of SS.

DETAILED DESCRIPTION OF THE INVENTION

Amplification of a cDNA that Encodes an SS

Figure 3A:
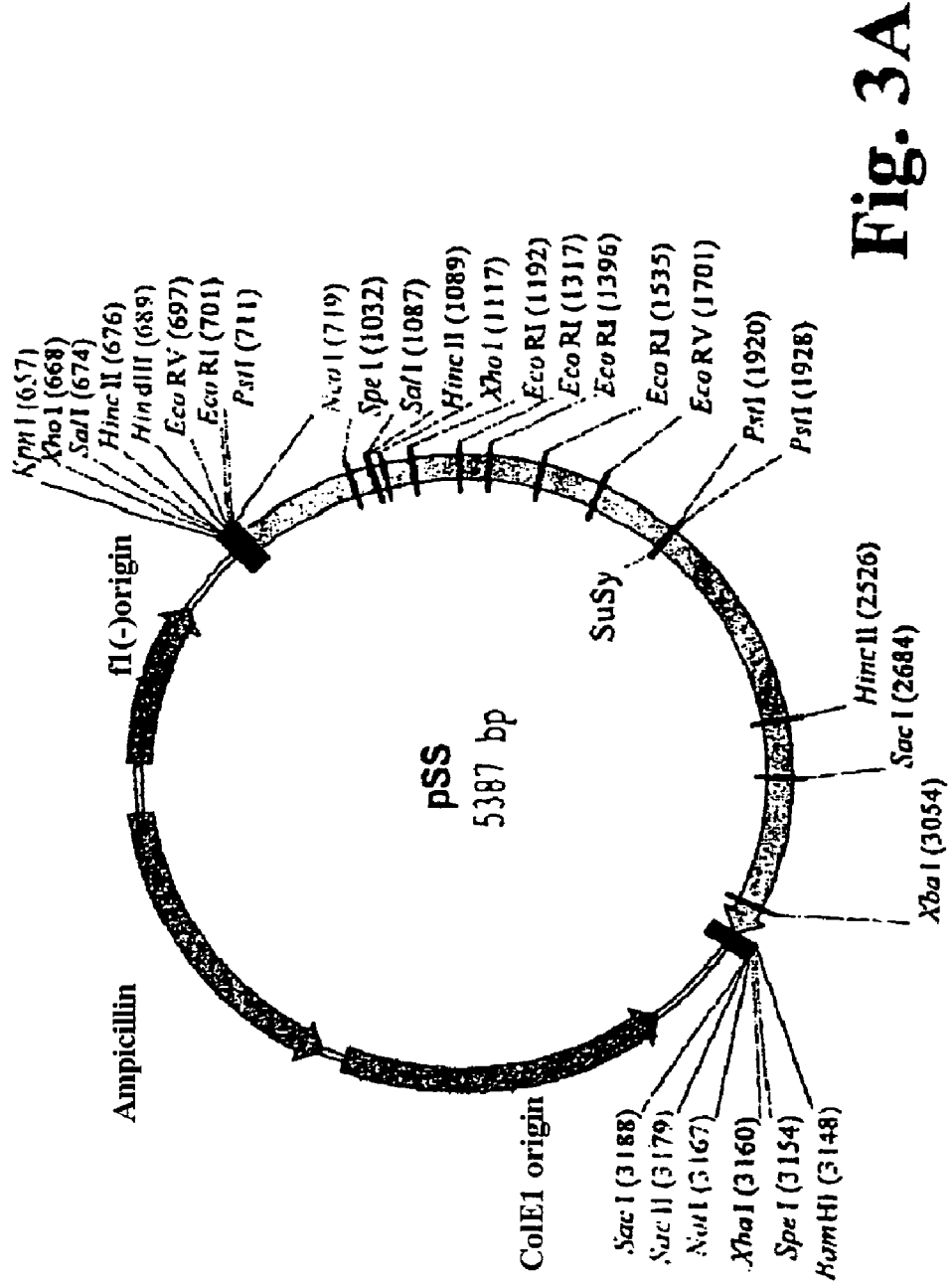

Knowing the nucleotide sequence of wild-type sucrose synthase SS4 (Fu, H., Park, W. D. (1995) Sink- and vascular-associated sucrose synthase functions are encoded by different gene classes in potato. Plant Cell 7, 1369-1385), two specific primers were created corresponding to the 5' and 3' ends of the gene. Using these primers, a 2418 base pair DNA fragment, designated SSX, from a potato-leaf cDNA library, was amplified by conventional PCR techniques. This PCR fragment was inserted in the pSK Bluescript plasmid (Stratagene), giving rise to the pSS construction (FIG. 3A), which was amplified in the host bacterium XL1 Blue.

Figure 3B:
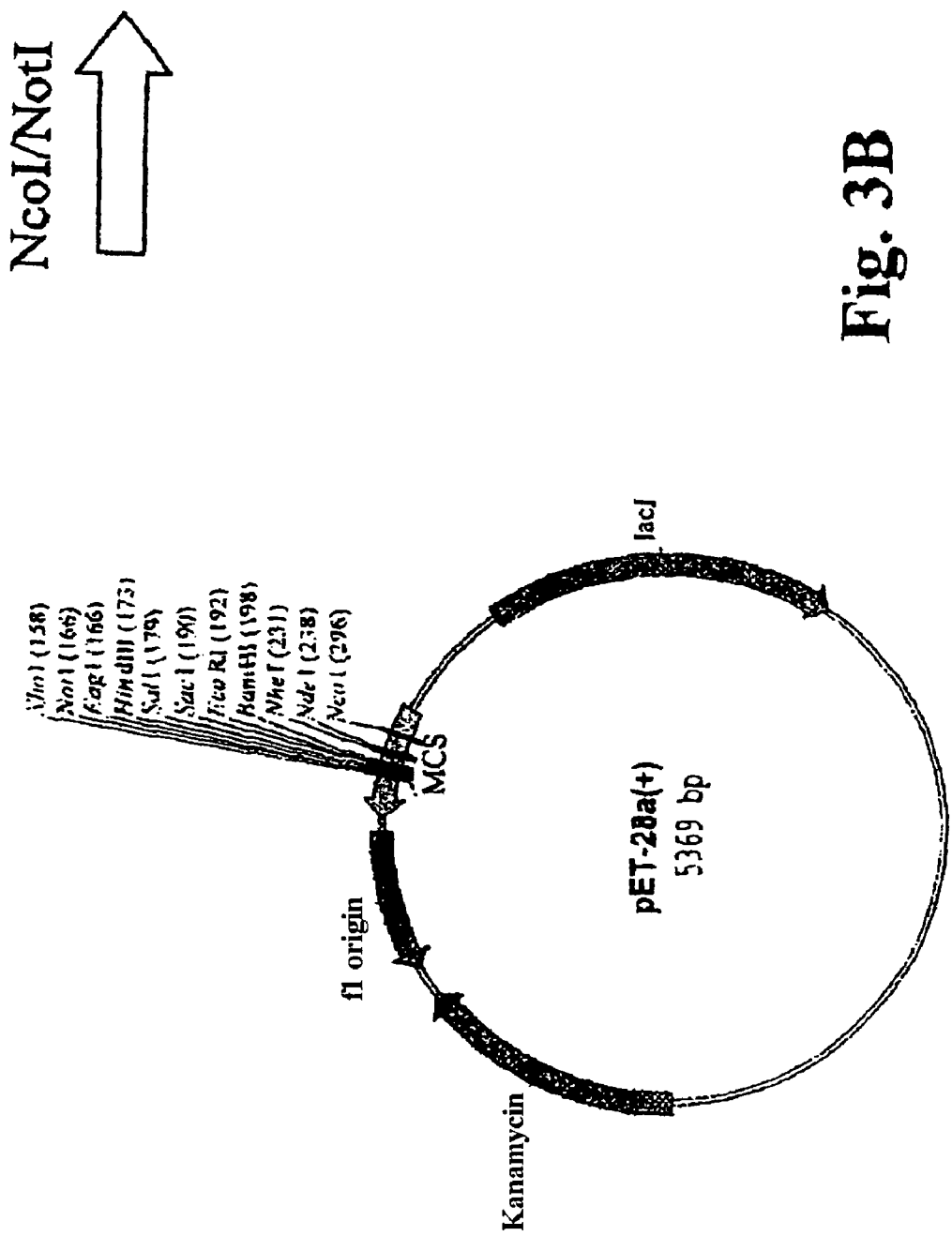
Figure 3C:
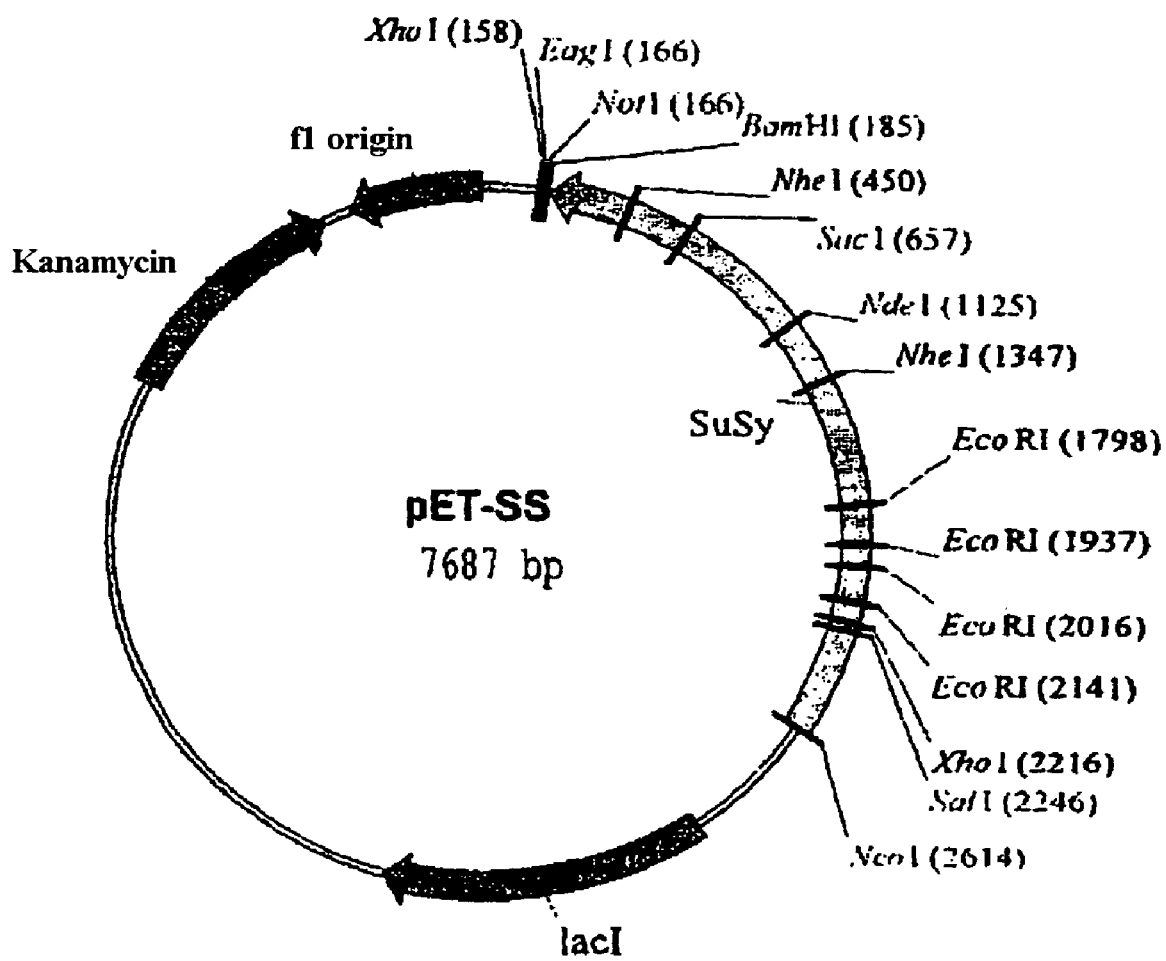

Production of Active Recombinant SS from a Special Strain of *E. Coli* pSS was digested with the NcoI and NotI restriction enzymes. The fragment released (which contains the cDNA encoding SS, SSX) was cloned on the same restriction sites of the pET-28a(+) expression plasmid (Novagen) (FIG. 3B) which possesses a nucleotide sequence in the polylinker region that encodes a histidine-rich sequence, which becomes fused with the recombinant protein. The resulting plasmid (designated pET-SS, FIG. 3C) was inserted by electroporation in various strains of *E. coli*. The *E. coli* strain BLR(DE3) (Novagen) transformed with pET-SS was deposited in the Spanish Type Culture Collection on 29 Oct. 2003, located in the Research Building of Valencia University, Burjassot Campus, Burjassot 46100 (Valencia, Spain) with the deposition number CECT:5850. The bacteria were incubated at 20° C. in LB medium. Overexpression of SSX was effected by addition of 1 mM isopropyl-β-D-thiogalactopyranoside (IPTG) in 100 ml of cell culture grown at 20° C. After six hours of induced culture, the bacteria were collected and resuspended in 4 ml of binding buffer (Novagen, His-bind purification kits), then sonicated and centrifuged at 40,000 g for 20 minutes. The supernatant, which contains the recombinant SS with an amino acid sequence rich in histidine residues at the N-terminal end, was passed through an affinity column of the His-bind protein purification kit from Novagen. Following the instructions with the kit, SS was eluted with 6 ml of the recommended elution buffer, which contained 200 mM of imidazole instead of 1 mol. After elution, the protein was quickly submitted to dialysis to remove any trace of imidazole, which inactivates SS irreversibly.

Production of an Isoform of SS Optimized for Production of ADPG

Using suitable primers, with pSS as template, the mutated variant SS5 was designed, giving rise to the construction pSS5. This was done using the QuikChange Site-Directed Mutagenesis kit (Stratagene). pSS5 was digested with NcoI and NotI. The fragment released (which contains SS5) was cloned on the same restriction sites of the pET-28a(+) expression plasmid giving rise to pET-SS5, which was inserted by electroporation in *E. coli* BLR(DE3). The *E. coli* strain XL1 Blue transformed with pSS5 was deposited in the Spanish Type Culture Collection on 29 Oct. 2003, located in the Research Building of Valencia University, Burjassot Campus, Burjassot 46100 (Valencia, Spain) with the deposition number CECT:5849.

Production of Transgenic Plants that Overexpress SS4

In the present invention SS was overexpressed (a) constitutively, (b) specifically in leaves and (c) specifically in storage organs such as tubers.

Figure 4A:
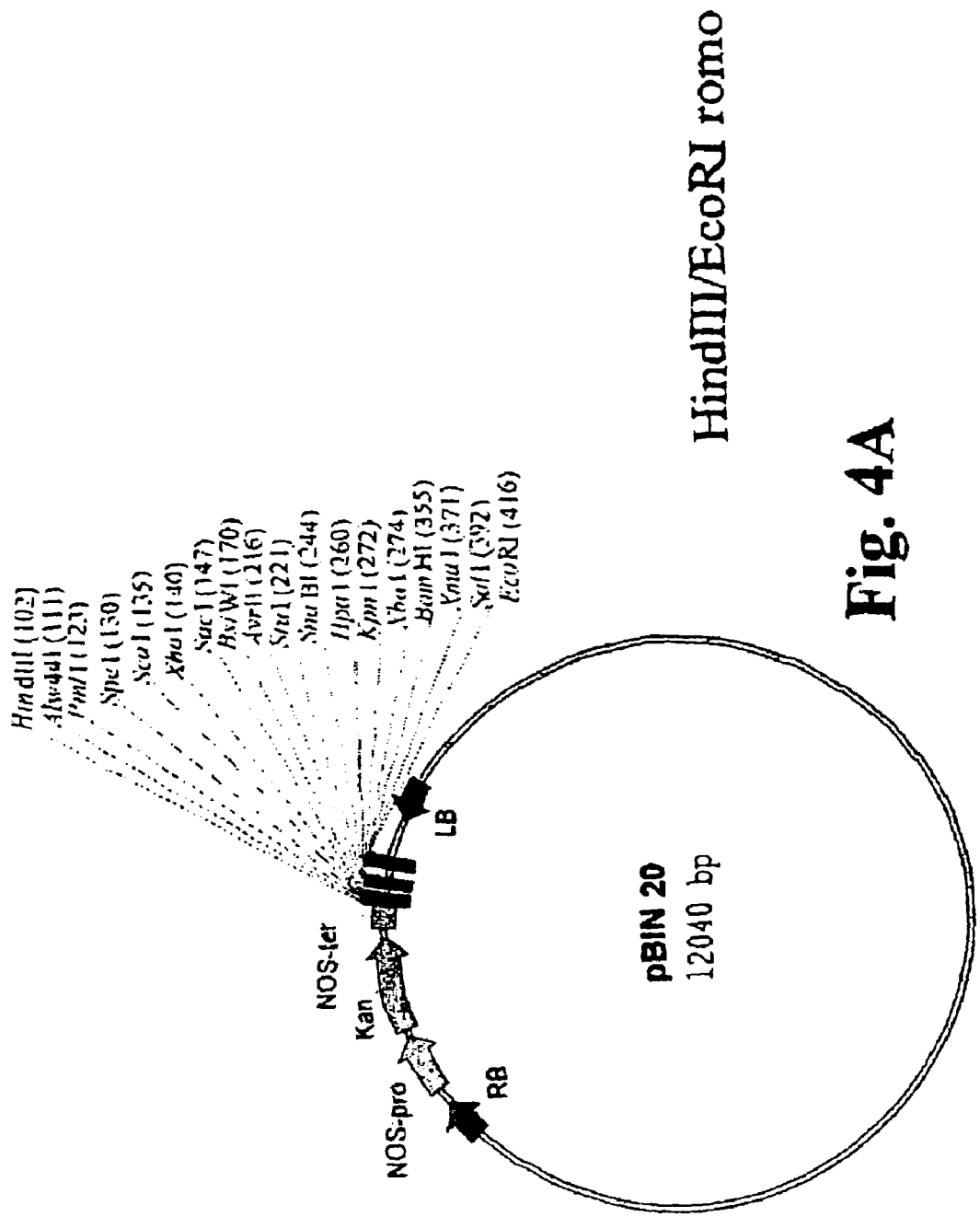
Figure 4B:
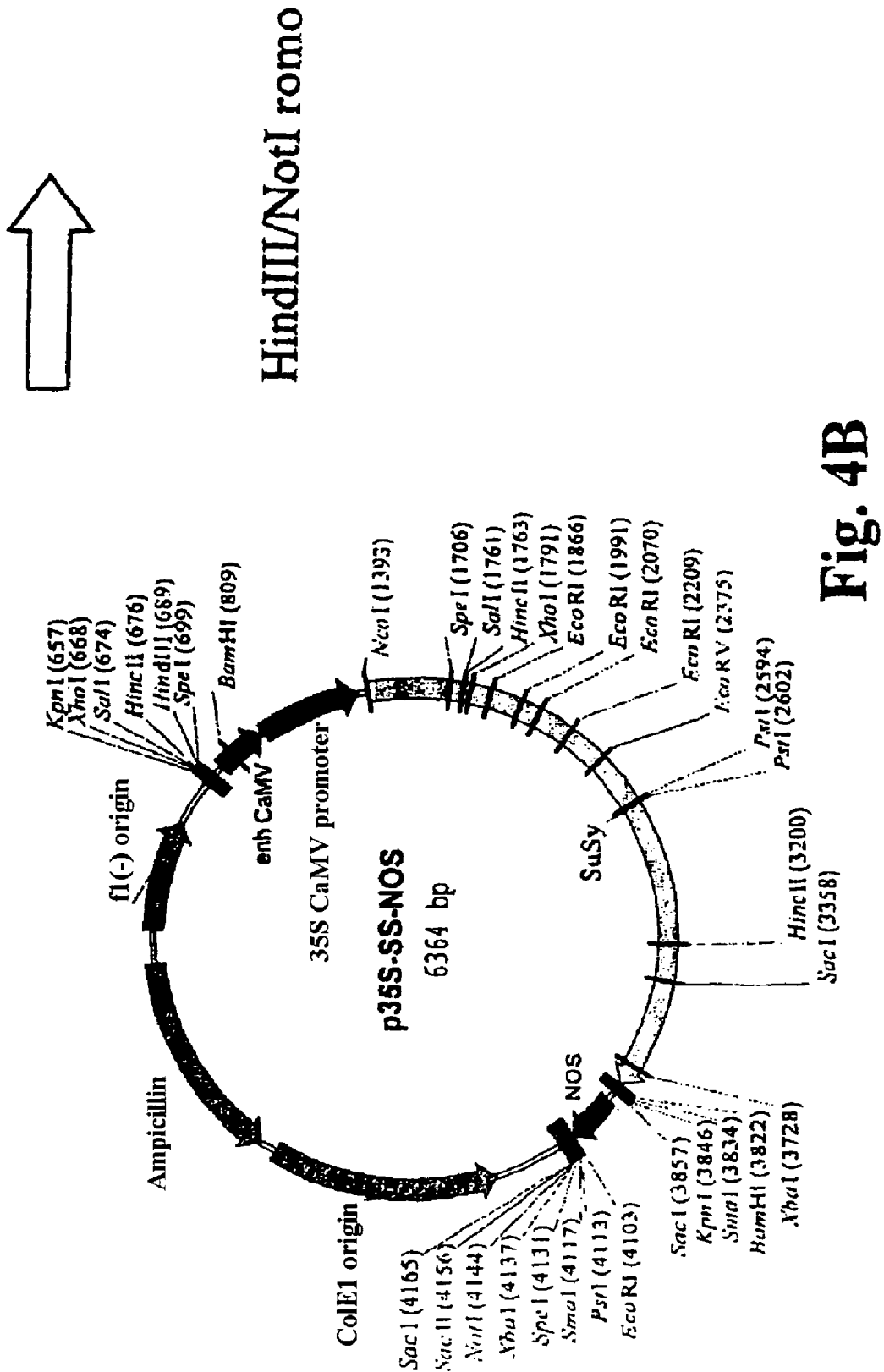

For the production of plants that overexpress SS constitutively, constructions were created that were controlled by the action of the 35S constitutive promoter of the tobacco mosaic virus. Successive insertion in pSS of the 35S promoter and NOS terminator in the 5' and 31 regions of SSX gave rise to the production of the plasmid p35S-SS-NOS, the restriction map of which is shown in FIG. 4B.

Figure 4C:
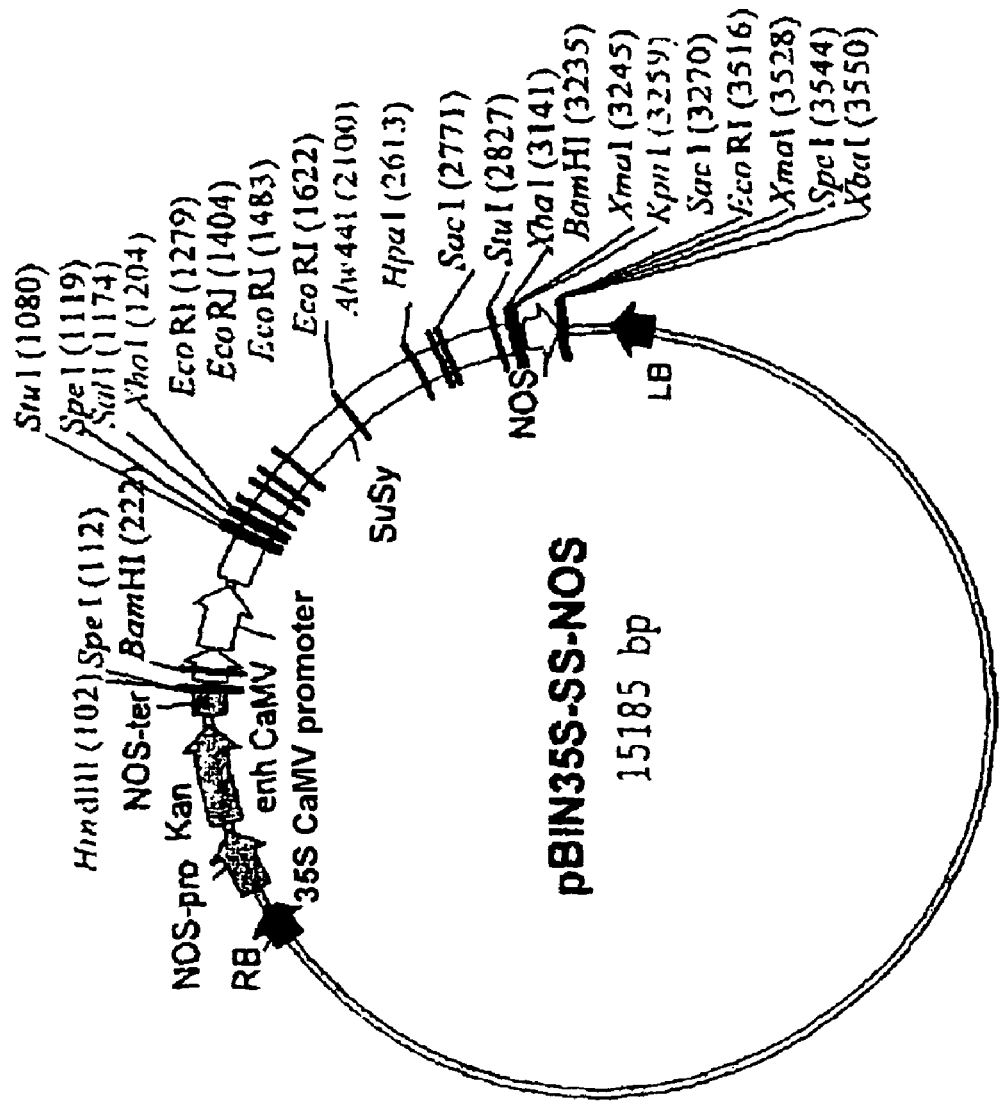

So as to be able to transfer this construction to the genome of the plants via *Agrobacterium tumefaciens*, it must first be cloned in a binary plasmid. For this, p35S-SS-NOS was digested successively with the enzymes NotI, T4 DNA polymerase and HindIII and was cloned within the binary plasmid pBIN20 (FIG. 4A) (Hennegan, K. P., Danna, K. J. (1998) pBIN20: An improved binary vector for *Agrobacterium*-mediated transformation. Plant Mol. Biol. Rep. 16, 129-131) which had previously been digested successively with the enzymes EcoRI, T4 DNA polymerase and HindIII. The plasmid thus obtained was designated pBIN35S-SS-NOS (FIG. 4C).

Figure 5A:
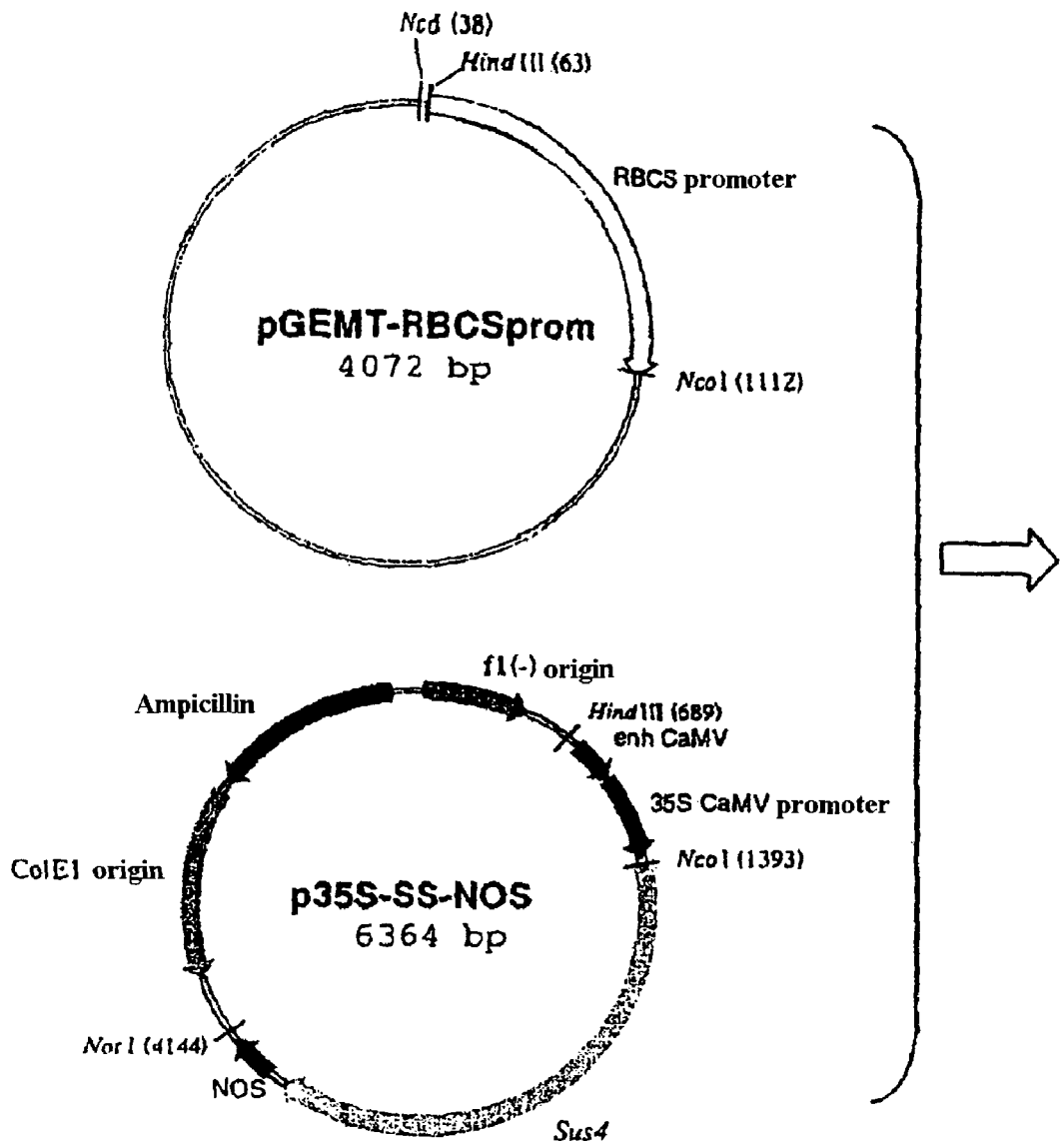
Figure 5B:
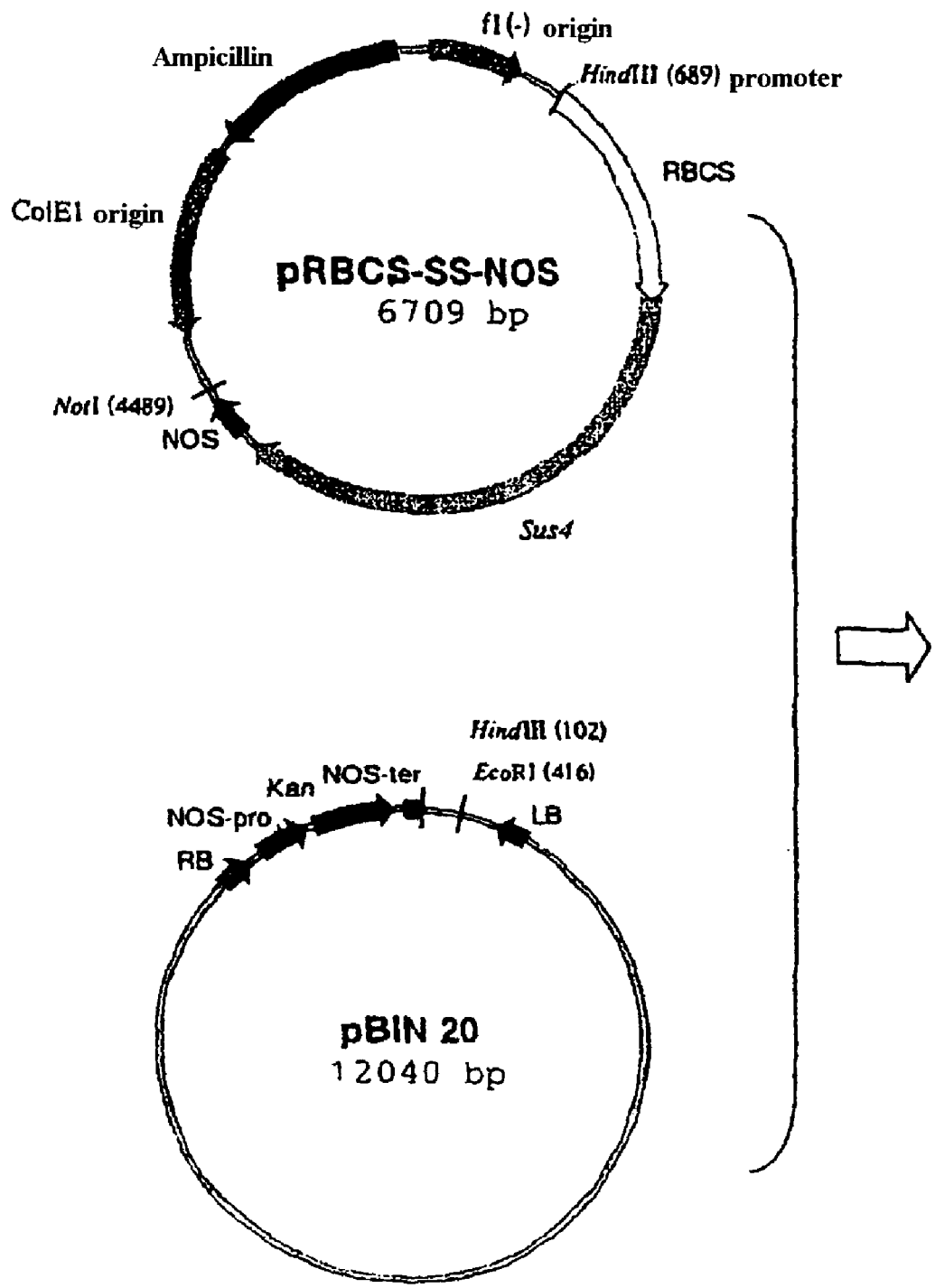
Figure 5C:
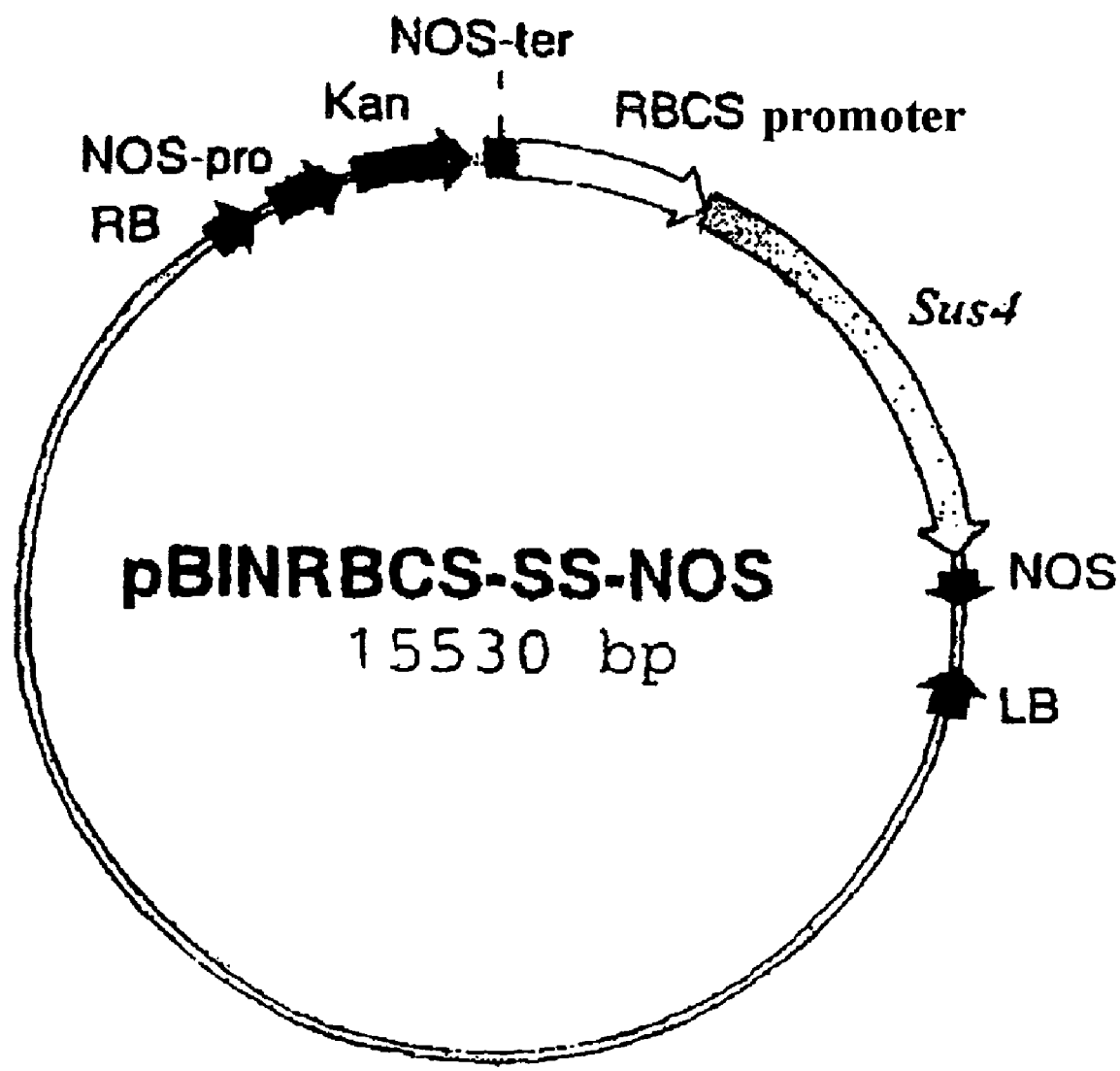

To overexpress SS specifically in illuminated leaves, PCR was used for amplifying the promoter region (designated RBCS) of the gene that encodes the small subunit of RUBISCO (ribulose-1,5-bisphosphate carboxylase/oxygenase) of tobacco (Barnes, S. A., Knight, J. S., Gray, J. C. (1994) Alteration of the amount of the chloroplast phosphate translocator in transgenic tobacco affects the distribution of assimilate between starch and sugar. Plant Physiol. 106, 1123-1129). This nucleotide sequence (which confers specific expression in photosynthetically active cells) was inserted in the pGEMT-easy vector (Promega), giving rise to pGEMT-RBCSprom (FIG. 5A). This construction was digested with HindIII and NcoI and the fragment released was cloned in the corresponding restriction sites of p35S-SS-NOS, giving rise to pRBCS-SS-NOS (FIG. 5B). This construction was digested successively with HindIII, T4 DNA polymerase and NotI. The fragment released was cloned in pBIN20 digested successively with HindIII, T4 DNA polymerase and EcoRI. The resulting construction was designated pBINRBCS-SS-NOS (FIG. 5C).

After being amplified in *E. coli* (XL1 Blue), both pBIN35S-SS-NOS and pBINRBCS-SS-NOS were inserted in *A. tumefaciens* C58:GV2260 (Debleare, R., Rytebier, B., de Greve, H., Debroeck, F., Schell, J., van Montagu, M., Leemans, J. (1985) "Efficient octopine Ti plasmid-derived vectors of *Agrobacterium* mediated gene transfer to plants" Nucl. Acids Res. 13, 4777-4788), which was used for transforming species such as tomato (*Lycopersicon sculentum*), tobacco (*Nicotiana tabacum*), potato (*Solanum tuberosum*) and rice by conventional techniques (Horsch, R. B., Fry, J. E., Hoffmann, N. L., Eichholtz, D., Rogers, S. G., Fraley, R. T. (1985) "A simple and general method for transferring genes into plants" Science 277, 1229-1231; Pozueta-Rṁomero, J., Houlné, G., Schantz, R., Chamarro, J. (2001) "Enhanced regeneration of tomato and pepper seedling explants for *Agrobacterium*-mediated transformation" Plant Cell Tiss. Org. Cult. 67, 173-180; Hiei, Y., Ohta, S., Komari, T., Kumashiro. T. (1994) "Efficient transformation of rice (*Oryza sativa* L.) mediated by *Agrobacterium* and sequence analysis of the boundaries of the T-DNA. Plant J. 6, 271-282). The strain of *A. tumefaciens* C58:GV2260 transformed with pBIN35S-SS-NOS was deposited in the Spanish Type Culture Collection on 29 Oct. 2003, located in the Research Building of Valencia University, Burjassot Campus, Burjassot 46100 (Valencia, Spain), with the deposition number CECT:5851.

Preparation of Assay Kits for Determination of Sucrose

One of the kits designed for the determination of sucrose, shown in the following Scheme I of enzymatic reactions involved in the kit for spectrophotometric/fluorimetric determination of sucrose based on the conversion of sucrose to a sugar nucleotide and then conversion of this to glucose-1-phosphate, glucose-6-phosphate and NAD(P)H.

Scheme I

Sucrose

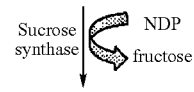

-continued
NDP-glucose

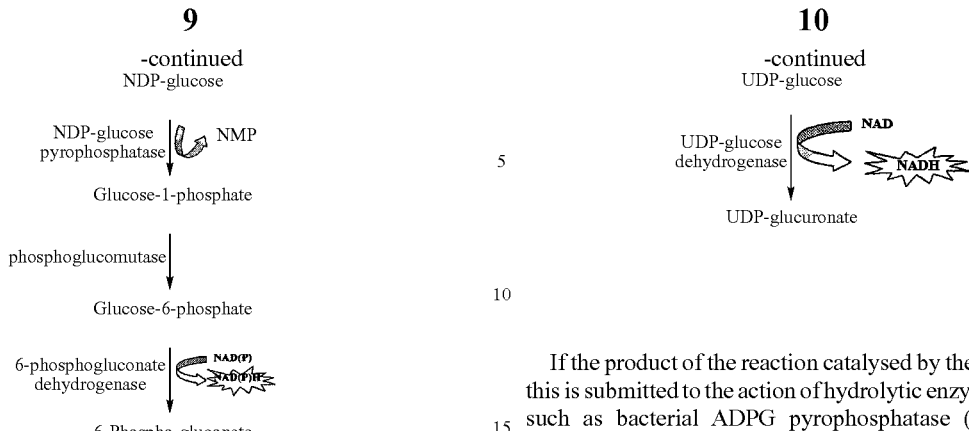

The kit is based on the action of SS on the sucrose molecule in the presence of a nucleotide diphosphate (e.g. UDP or ADP), releasing equimolar amounts of fructose and the corresponding sugar nucleotide. If the sugar nucleotide resulting from the reaction is UDPG, this is submitted to the action of hydrolytic enzymes of UDPG such as UDPG pyrophosphatase of the Nudix type (EC 3.6.1.45) (Yagi, T., Baroja-Fernández, E., Yamamoto, R., Muñoz, F. J., Akazawa, T., Pozueta-Rṁomero, J. (2003) Cloning, expression and characterization of a mammalian Nudix hydrolase-like enzyme that cleaves the pyrophosphate bond of UDP-glucose. Biochem. J. 370, 409-415) or UDPG hydrolase (Burns, D. M., Beacham, I. R. (1986) Nucleotide sequence and transcriptional analysis of the E. coli ushA gene, encoding periplasmic UDP-sugar hydrolase (5'-nucleotidase): regulation of the ushA gene, and the signal sequence of its encoded protein product. Nucl. Acids Res. 14, 4325-4342). The G1P released by the action of these hydrolytic enzymes is transformed by the action of phosphoglucomutase (PGM), yielding glucose-6-phosphate (G6P), which in its turn can be made to undergo a coupling reaction with NAD(P)+ by the action of the enzyme G6P dehydrogenase (G6PDH), producing 6-phosphogluconate and NAD(P)H, which can easily be determined by fluorimetry and by spectrophotometry at 340 nm. In its turn, the NAD(P)H released can be coupled to the action of FMN-oxidoreductase/luciferase, yielding light, which is quantified spectrophotometrically.

Alternatively, as shown in scheme II, the UDPG produced can be coupled with UDPG dehydrogenase (EC 1.1.1.22) which, in the presence of NAD, gives rise to equimolar amounts of UDP-glucuronate and NADH, which can be determined by fluorimetry or by spectrophotometry at 340 nm. In its turn, the NADH released can be coupled to the action of FMN-oxidoreductase/luciferase, yielding light, which is quantified spectrophotometrically.

Scheme II

Sucrose

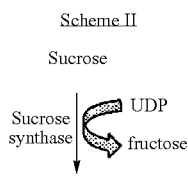

-continued
UDP-glucose

If the product of the reaction catalysed by the SS is ADPG, this is submitted to the action of hydrolytic enzymes of ADPG such as bacterial ADPG pyrophosphatase (EC 3.6.1.21) (Moreno-Bruna, B., Baroja-Fernández, E., Muñnoz, F. J., Bastarrica-Berasategui, A., Zandueta-Criado, A., Rodríguez-López, M., Lasa, I., Akazawa, T., Pozueta-Romero, J. (2001) Adenosine diphosphate sugar pyrophosphatase prevents glycogen biosynthesis in Escherichia coli. Proc. Natl. Acad. Sci. USA 98, 8128-8132). The G1P released is transformed by the action of phosphoglucomutase, yielding glucose-6-phosphate (G6P), which can in turn be made to undergo a coupling reaction with NAD(P)+ by the action of the enzyme G6P dehydrogenase, producing 6-phosphogluconate and NAD(P)H, which can easily be determined by fluorimetry or spectrophotometry at 340 nm.

In any case, the schemes of enzymatic reactions coupled to the production of a sugar nucleotide mediated by SS are perfectly suitable for application to amperometric detection.

EXAMPLES OF CARRYING OUT THE INVENTION

Examples are described below, which show in detail the procedure for cloning a cDNA that encodes an isoform of SS of potato in a suitable expression vector and in a strain of E. coli optimized for the production and accumulation of the enzyme in its active form. Other examples describe the use of the recombinant SS for making assay kits for the determination of sucrose in plant samples, serum, urine, fruit juices, sweetened fruit drinks, refreshing drinks, etc. Another example describes the use of variants of SS optimized for the large-scale production of sugar nucleotides such as UDPG and ADPG. Finally, another example describes the production of plants with high content of sucrose, ADPG and starch and a high amylose/amylopectin ratio as a result of the high ADPG-producing activity in plants that overexpress SS.

EXAMPLE 1

Expression, in Escherichia coli BLR (DE3), of a Recombinant SS with a Histidine Tail, which can be Purified Easily and has High Specific Activity Knowing the nucleotide sequence of the SS4 gene that encodes an isoform of SS of potato, it was possible to create two specific primers whose sequences are, in the 5'-3' direction, SEQ ID NO: 1 and SEQ ID NO: 2. Using these primers, a DNA fragment, designated as SSX, was amplified by conventional methods of PCR, from a potato tuber cDNA library, and this was inserted in a pSK Bluescript plasmid (Stratagene), which was amplified in the host bacterium XL1 Blue. The nucleotide sequence of SSX is SEQ ID NO: 3, which is slightly different from SS4 (GenBank accession number U24087). The amino acid sequence deducted from SEQ ID NO: 3 is slightly different from SS4 and is therefore designated SSX. The amino acid sequence deducted after expression of SEQ ID NO: 3 in the pET-28a(+) plasmid is SEQ ID NO: 4, which includes a histidine-rich sequence of 38 amino acids fused with the amino-terminal end of the amino acid sequence deducted from SEQ ID NO: 3.

Figure 6:
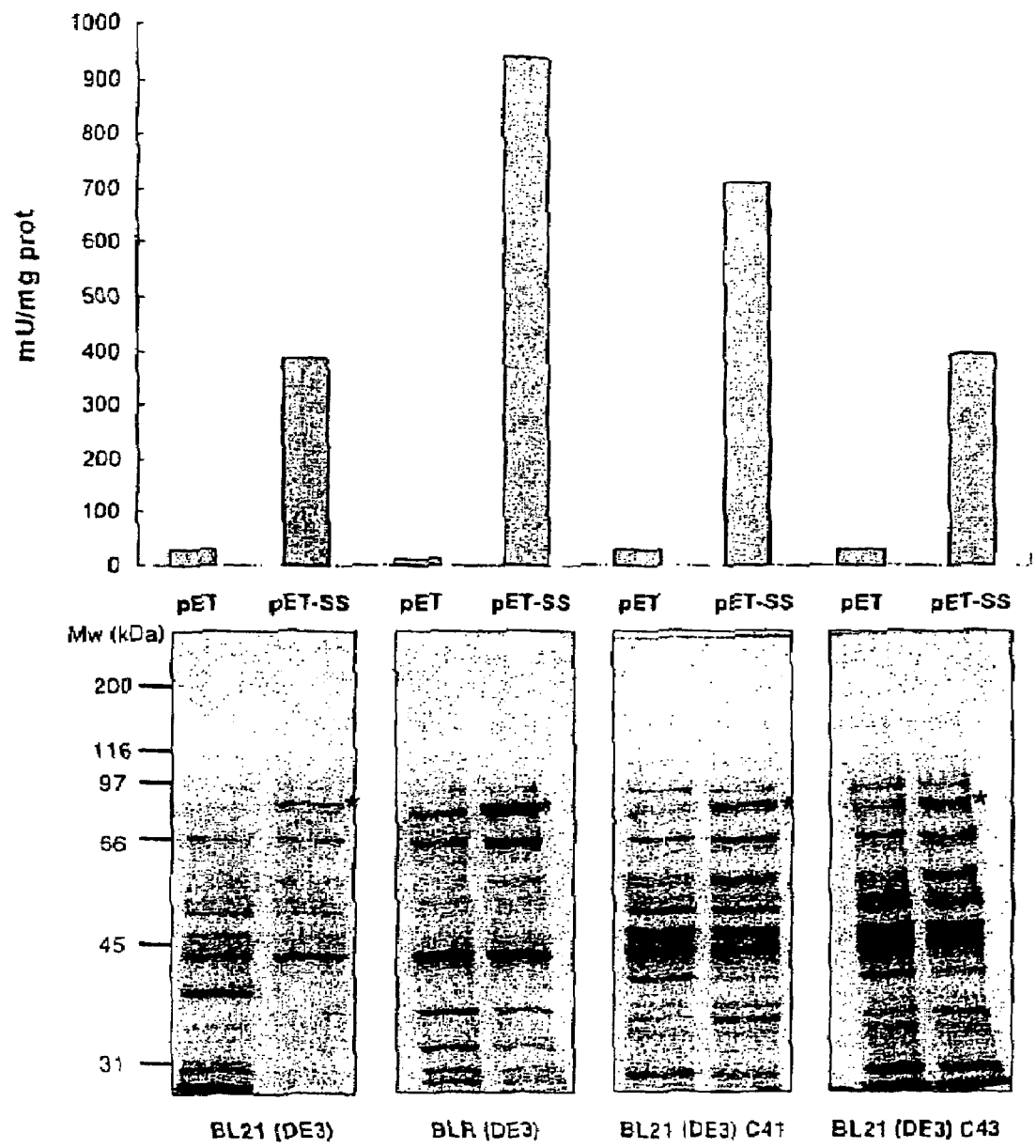

Production of SSX in BL21(DE3) bacteria transformed with pET-SS was induced on adding 1 mM IPTG. After six additional hours of culture at 37° C., it was observed that the bacteria transformed with pET-SS accumulated a protein in aggregated form, the size of which corresponds to SS. However, these bacteria did not have SS activity. This failure in the expression of an active form of SS can be attributed to the problems that E. coli has in the correct folding of certain eukaryotic proteins of high molecular weight (Miroux, B., Walker, J. E. (1996) "Over-production of proteins in Escherichia coli: mutant hosts that allow synthesis of some membrane proteins and globular proteins at high levels" J. Mol. Biol. 260, 289-298). With the aim of overcoming this problem, the capacity for production of active SS in other bacterial strains and at a temperature of 20° C. was investigated. In all of them, production of SSX was induced on adding 1 mM of IPTG. After 6 hours of additional incubation, the bacteria were sonicated and centrifuged. The resulting supernatant was analysed for SS activity. In these conditions, as shown in FIG. 6, the BLR(DE3) strain proved to be the most efficient from the standpoint of production of soluble, active SS. The E. coli strain BLR(DE3) (Novagen) transformed with pET-SS was deposited in the Spanish Type Culture Collection on 29 Oct. 2003, with the deposition number CECT:5850. The contribution of recombinant SSX in the total protein pool of CECT:5850 is approximately 20%, compared to the very low productivity of recombinant SS (30 micrograms per gram of bacteria) described in the literature (Nakai, T., Tonouchi, N., Tsuchida, T., Mori, H., Sakai, F., Hayashi, T. (1997) "Expression and characterization of sucrose synthase from mung bean seedlings in Escherichia Coli" Biosci. Biotech. Biochem. 61, 1500-1503; Li, C. R., Zhang, X. B., Hew, C. S. (2003) "Cloning, characterization and expression analysis of a sucrose synthase gene from tropical epiphytic orchid Oncidium goldiana. Physiol. Plantarum 118, 352-360). The supernatant was passed through the His-Bind affinity column (Novagen), in which the recombinant protein possessing a histidine tail is retained specifically. After eluting and dialysing the purified SS, it was incubated with 50 mM HEPES, pH 7.0/1 mM EDTA/20% polyethylene glycol/1 mM MgCl$_2$/15 mM KCl/2 mM UDP. The specific activity, determined in terms of production of UDPG, was 80 units/mg of protein, much higher than the activity of 0.05-5 units/mg of recombinant SS described in the literature (Nakai, T., Tonouchi, N., Tsuchida, T., Mori, H., Sakai, F., Hayashi, T. (1997) "Expression and characterization of sucrose synthase from mung bean seedlings in Escherichia coli" Biosci. Biotech. Biochem. 61, 1500-1503; Li, C. R., Zhang, X. B., Hew, C. S. (2003) "Cloning, characterization and expression analysis of a sucrose synthase gene from tropical epiphytic orchid Oncidium goldiana. Physiol. Plantarum 118, 352-360); Römer, U., Schrader, H., Günther, N., Nettelstroth, N., Frommer, W. B., Elling, L. (2004) Expression, purification and characterization of recombinant sucrose synthase I from Solanum tuberosum L. for carbohydrate engineering. J. Biotechnology 107, 135-149) and greater than 3 units/mg corresponding to the SS purified from plant extracts (Pressey R (1969) Potato sucrose synthase: purification, properties, and changes in activity associated with maturation. Plant Physiol. 44, 759-764. The unit is defined as the amount of enzyme that catalyses the production of one micromol of UDPG per minute. The affinity for UDP in the presence of 500 mM sucrose was Km(UDP)=0.25 mM, whereas the Km for sucrose was 30 mM in the presence of 1 mM UDP. This affinity for sucrose in the presence of UDP is significantly higher than that exhibited by the recombinant SS obtained in yeasts (Km=95 mM, Römer, U., Schrader, H., Günther, N., Nettelstroth, N., Frommer, W. B., Elling, L. (2004) Expression, purification and characterization of recombinant sucrose synthase I from Solanum tuberosum L. for carbohydrate engineering. J. Biotechnology 107, 135-149).

EXAMPLE 2

Large-Scale Production of UDPG and ADPG Based on the Use of Recombinant SS from E. Coli Three grams of UDPG of high purity was produced efficiently and economically after incubation for 12 hours at 37° C. of 100 milliliters of a solution containing 1 M sucrose, 50 mM HEPES, pH 7.0/1 mM EDTA/20% polyethylene glycol/1 mM MgCl$_2$/15 mM KCl/100 mM UDP and 30 units of recombinant SS from potato obtained after expression of PET-SS in BLR(DE3) and subsequent purification. Reaction came to an end after heating the solution at 100° C. for 90 seconds and then centrifugation at 10,000 g for 10 minutes. The supernatant was applied to a preparative-scale HPLC chromatograph (Waters Associates) and the UDPG was purified as described in the literature (Rodríguez-López, M., Baroja-Fernández, E., Zandueta-Criado, A., Pozueta-Romero, J. (2000) Adenosine diphosphate glucose pyrophosphatase: a plastidial phosphodiesterase that prevents starch biosynthesis. Proc. Natl. Acad. Sci. USA 97, 8705-8710).

Production of ADPG required the generation of a mutated form of SS with an affinity for ADP much greater than that described for the SS extracted from plant tissues (Pressey R (1969) Potato sucrose synthase: purification, properties, and changes in activity associated with maturation. Plant Physiol. 44, 759-764; Nguyen-Quock, B., Krivitzky, M., Huber, S. C., Lecharny, A. (1990) Sucrose synthase in developing maize leaves. Plant Physiol. 94, 516-523; Morell, M., Copeland, L. (1985) Sucrose synthase of soybean nodules. Plant Physiol. 78, 149-154).

This isoform, designated SS5, was obtained by point mutagenesis of SSX using the QuikChange Site-Directed Mutagenesis kit (Stratagene) and successive use of the following pairs of primers whose sequences are [SEQ ID NO: 5, SEQ ID NO: 6], [SEQ ID NO: 7, SEQ ID NO: 8] and [SEQ ID NO: 9, SEQ ID NO: 10]. The nucleotide sequence obtained, designated SS5, is SEQ ID NO: 11. The changes in the amino acid sequence of SS5 (Susy 5) relative to SS4-Susy 4-(present in databases) are shown shaded in Table I. The amino acid sequence deducted after expression of SEQ ID NO: 11 in the pET-28a(+) plasmid is SEQ ID NO: 12, which includes a histidine-rich sequence of 38 amino acids fused with the amino-terminal end of the amino acid sequence deducted from SEQ ID NO: 11.

Table I includes said histidine-rich sequence of 38 amino acids fused to the amino-terminal portion of SS5.

TABLE I

```
  1  - - - - - - - - - - - - - - - - - - - - - - - - - - - - - -  SuSy 4
  1  M G S S H H H H H H S S G L V P R G S H M A S M T G G Q Q M  SuSy 5
  2  - - - - - - - M A E R V L T R V H S L R E R V D A T L A A H R  SuSy 4
 31  G R K S S E F M A E R V L T R V H S L R E R V D A T L A A H R  SuSy 5
 25  N E I L L F L S R I E S H G K G I L K P H E L L A E F D A I    SuSy 4
 61  N E I L L F L S R I E S H G K G I L K P H E L L A E F D A I    SuSy 5
 55  R Q D D K N K L N E H A F E E L L K S T Q E A I V L P P W V    SuSy 4
 91  R Q D D K N K L N E H A F E E P L K S T Q E A I V L P P W V    SuSy 5
 85  A L A I R L R P G V W E Y I R V N V N A L V V E E L S V P E    SuSy 4
121  A L A I R L R P G V W E Y I R V N V N A L V V E E L S V P E    SuSy 5
115  Y L Q F K E E L V D G A S N G N F V L E L D F E P F T A S F    SuSy 4
151  Y L Q F K E E L V D G A S N G N F V L E L D F E P F T A S F    SuSy 5
145  P K P T L K S I G N G V E F L N R H L S A K M F H D K E S      SuSy 4
181  P K P T L K S I G N G V E F L N R H L S A K M F H D K E S      SuSy 5
175  M T P L L E F L R A H H Y K G K T M M L N D R I Q N S N T L    SuSy 4
211  M T P L L E F L R A H H Y K G K T M M L N D R I Q N S N T L    SuSy 5
205  Q N V L R K A E E Y L I M L P P E T P Y F E F E H K F Q E I    SuSy 4
241  Q N V L R K A E E Y L I M L S P D T P Y F E F E H K F Q E I    SuSy 5
235  G L E K G W G D T A E R V L E M V C M L L D L L E A P D S C    SuSy 4
271  G L E K G W G D T A E R V L E M V C M L L D L L E A P D S C    SuSy 5
265  T L E K F L G R I P M V F N V V I L S P H G Y F A Q E N V L    SuSy 4
301  T L E K F L G R I P M V F N V V I L S P H G Y F A Q E N V L    SuSy 5
295  G Y P D T G G Q V V Y I L D Q V P A L E R E M L K R I K E Q    SuSy 4
331  G Y P D T G G Q V V Y I L D Q V P A L E R E M L K R I K E Q    SuSy 5
325  G L D I I P R I L I V T R L L P D A V G T T C G Q R I E K V    SuSy 4
361  G L D I I P R I L I V T R L L P D A V G T T C G Q R I E K V    SuSy 5
355  Y G A E H S H I L R V P F R T E K G I V R K W I S R F E V W    SuSy 4
391  Y G A E H S H I L R V P F R T E K G I V R K W I S R F E V W    SuSy 5
385  P Y M E T F I E D V A K E I S A E L Q A K P D L I I G N Y S    SuSy 4
421  P Y M E T F I E D V A K E I S A E L Q A K P D L I I G N Y S    SuSy 5
415  E G N L A A S L L A H K L G V T Q C T I A H A L E K T K Y P    SuSy 4
451  E G N L A A S L L A H K L G V T Q C T I A H A L E K T K Y P    SuSy 5
445  D S D I Y W K K F D E K Y H F S S Q F T A D L I A M N H T D    SuSy 4
481  D S D I Y W K K F D E K Y H F S S Q F T A D L I A M N H T D    SuSy 5
475  F I I T S T F Q E I A G S K D T V G Q Y E S H M A F T M P G    SuSy 4
511  F I I T S T F Q E I A G S K D T V G Q Y E S H M A F T M P G    SuSy 5
505  L Y R V V H G I N V F D P K F N I V S P G A D I N L Y F S Y    SuSy 4
541  L Y R V V H G I N V F D P K F N I V S P G A D I N L Y F S Y    SuSy 5
535  S E T E K R L T A F H P E I D E L L Y S D V E N D E H L C V    SuSy 4
571  S E T E K R L T A S H P E I D E L L Y S D V E N D E H L C V    SuSy 5
565  L K D R T K P I L F T M A R L D R V K N L T G L V E W Y A K    SuSy 4
601  L K D R T K P I L F T M A R L D R V K N L T G L V E W Y A K    SuSy 5
595  N P R L R G L V N L V V V G G D R R K E S K D L E E Q A E M    SuSy 4
631  N P R L R G L V N L V V V G G D R R K E S K D L E E Q A E M    SuSy 5
625  K K M Y E L I E T H N L N G Q F R W I S S Q M N R V R N G E    SuSy 4
661  K K M Y E L I E T H N L N G Q F R W I S S Q M N R V R N G E    SuSy 5
655  L Y R Y I A D T K G A F V Q P A F Y E A F G L T V V E A M T    SuSy 4
691  L Y R Y I A D T K G A F V Q P A F Y E A F G L T V V E A M T    SuSy 5
685  C G L P T F A T N H G G P A E I I V H G K S G F H I D P Y H    SuSy 4
721  C G L P T F A T N H G G P A E I I V H G K S G F H I D P Y H    SuSy 5
715  G E Q A A D L L A D F F E K C K K D P S H W E T I S M G G L    SuSy 4
751  G E Q A A D L L A D F F E K C K K D P S H W E T I S T D G L    SuSy 5
745  K R I E E K Y T W Q I Y S E S L L T L A A V Y G F W K H V S    SuSy 4
781  K R I Q E K Y T W Q I Y S E R L L T L A A V Y G F W K H V S    SuSy 5
775  K L D R L E I R R Y L E M F Y A L K Y R K M A E A V P L A A    SuSy 4
811  K L D R L E I R R Y L E M F Y A L K Y R K M A E A V P L A A    SuSy 5
805  E                                                              SuSy 4
841  E                                                              SuSy 5
```

The recombinant SS5 obtained after expression of pET-SS5 had a Vmax of 80 units/mg of protein and 65 units/mg of protein in the presence of UDP and ADP, respectively. The affinities for UDP and ADP in the presence of 500 mM sucrose were very similar (Km=0.2 mM both for ADP and for UDP), whereas the Km for sucrose was 30 mM and 100 mM in the presence of saturated concentrations of UDP and ADP, respectively. These kinetic parameters are very different from those described for the SS extracted from potato tuber and other organs of other species, according to which the Vmax of the enzyme is 10 times higher in the presence of UDP than in the presence of ADP (Pressey R (1969) Potato sucrose synthase: purification, properties, and changes in activity associated with maturation. Plant Physiol. 44, 759-764; Morell, M., Copeland, L. (1985) Sucrose synthase of soybean nodules. Plant Physiol. 78, 149-154; Nguyen-Quock, B., Krivitzky, M., Huber, S.C., Lecharny, A. (1990) Sucrose synthase in developing maize leaves. Plant Physiol. 94, 516-523). The E. coli strain XL1 Blue transformed with pSS5 was deposited in the Spanish Type Culture Collection, with the deposition number CECT:5849.

Three grams of ADPG of high purity was produced efficiently and economically after incubation for 12 hours at 37° C. of 100 milliliters of a solution containing 1 M sucrose, 50 mM HEPES, pH 7.0/1 mM EDTA/20% polyethylene glycol/1 mM MgCl$_2$/15 mM KCl/100 mM ADP and 30 units of recombinant SS from potato obtained after expression of pET-SS5 in BLR(DE3) and subsequent purification in a His-bind column. Reaction came to an end after heating the solution at 100° C. for 90 seconds and then centrifugation at 10,000 g for 10 minutes. The supernatant was applied to a preparative-scale HPLC chromatograph (Waters Associates) for purification of the ADPG.

EXAMPLE 3

Preparation of Enzymatic Kits for Determination of Sucrose

For determination of sucrose, the following reaction cocktails were prepared with the following components and final amounts/concentrations:

1. Kits Based on the Use of Hydrolytic Enzymes of Sugar Nucleotides:
   a. 2 units of SS (recombinant or not)
   b. 2 mM of ADP or UDP (depending on whether ADPG or UDPG is being produced, respectively)
   c. 2 units of ADPG pyrophosphatase or 2 units of UDPG pyrophosphatase (depending on whether it is to be included in the ADP or UDP reaction cocktail, respectively)
   d. 2 units of PGM
   e. 2 units of G6PDH
   f. 0.5 mM of NAD(P)
   g. reaction buffer: 50 mM HEPES, pH 7.0/1 mM EDTA/20% polyethylene glycol/1 mM $MgCl_2$/15 mM KCl
   h. previously filtered test sample
2. Kit Based on the Use of UDPG Dehydrogenase
   a. 2 units of SS (recombinant or not)
   b. 2 mM of UDP
   c. 2 units of UDPG dehydrogenase
   d. 0.5 mM of NAD
   e. reaction buffer: 50 mM HEPES, pH 7.0/1 mM EDTA/20% polyethylene glycol/1 mM $MgCl_2$/15 mM KCl
   f. previously filtered test sample Determination of the amount of sucrose present in the test sample is based on fluorimetric determination or spectrophotometric determination (at 340 nm) of the NAD(P)H produced according to the coupled reactions shown in schemes I and II.

For determining the sucrose content of barley seeds with different degrees of development (FIG. 7), the reactions took place in 300-microliter wells of an ELISA plate for 3 minutes at 37° C. The volume of the test sample was 20 microliters, and the volume of the cocktail resulting from combination of reagents a-g (kit #1) and a-e (kit #2) was 280 microliters. The blanks contained all the components of the cocktail except SS. Measurement was carried out with a MultiSkan spectrophotometer. The values obtained, both with the kit of type "1" and with the kit of type "2" were found to be comparable to those determined using chromatographic techniques described in the introduction (Baroja-Fernández, E., Muñoz, F. J., Saikusa, T., Rodríguez-López, M., Akazawa, T., Pozueta-R momero, J. (2003) Sucrose synthase catalyzes the de novo production of ADPglucose linked to starch biosynthesis in heterotrophic tissues of plants. Plant Cell Physiol. 44, 500-509).

EXAMPLE 4

Production of Transgenic Plants that Overexpress SS

Figure 8:
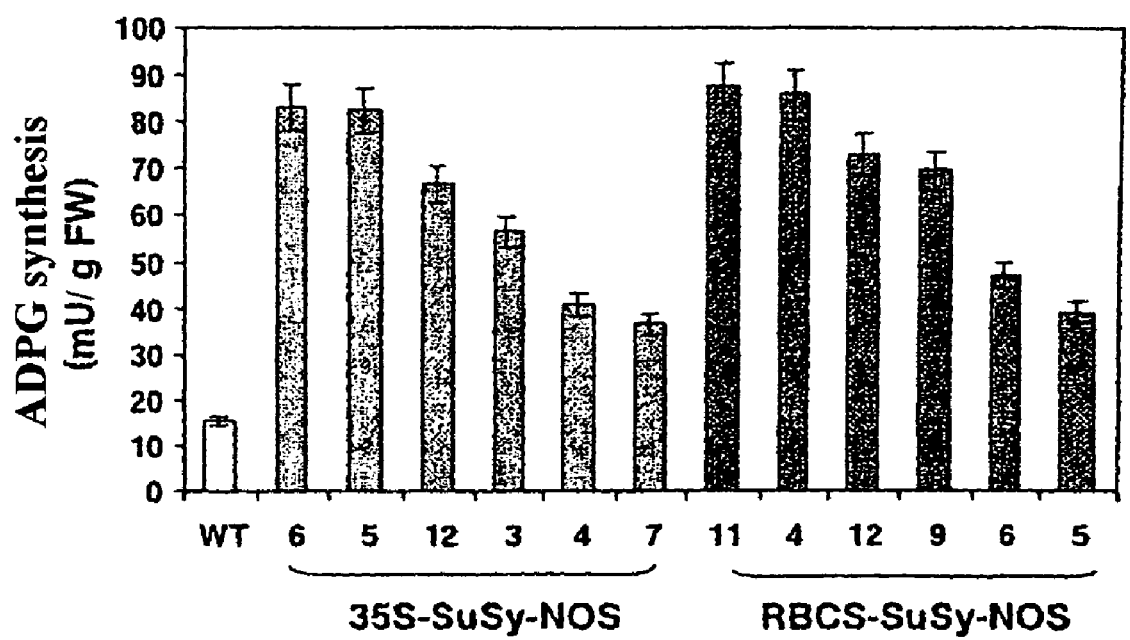
Figure 9:
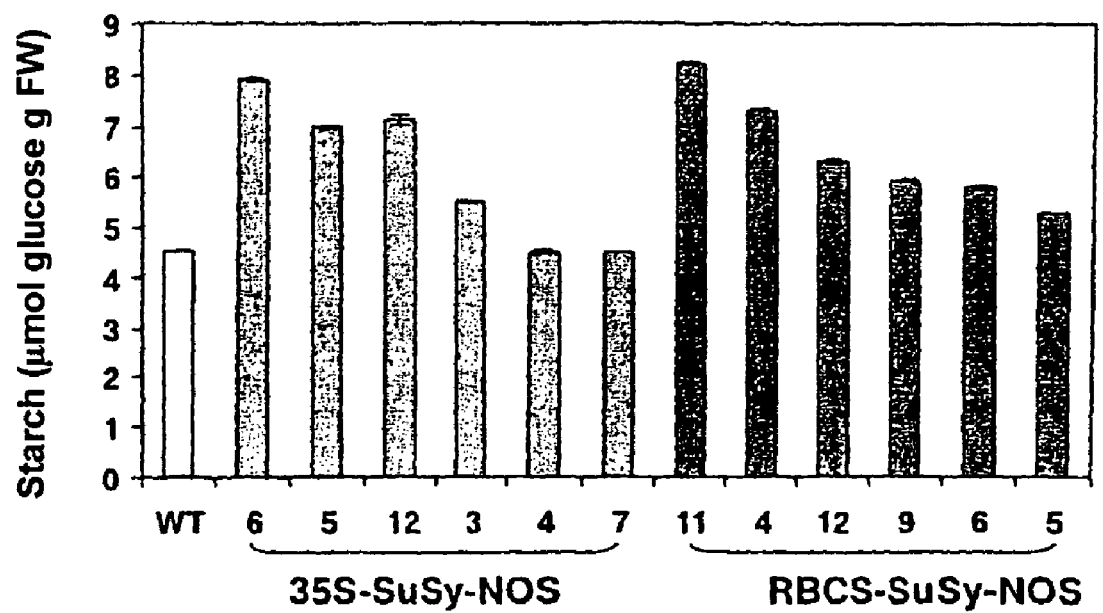
Figure 10:
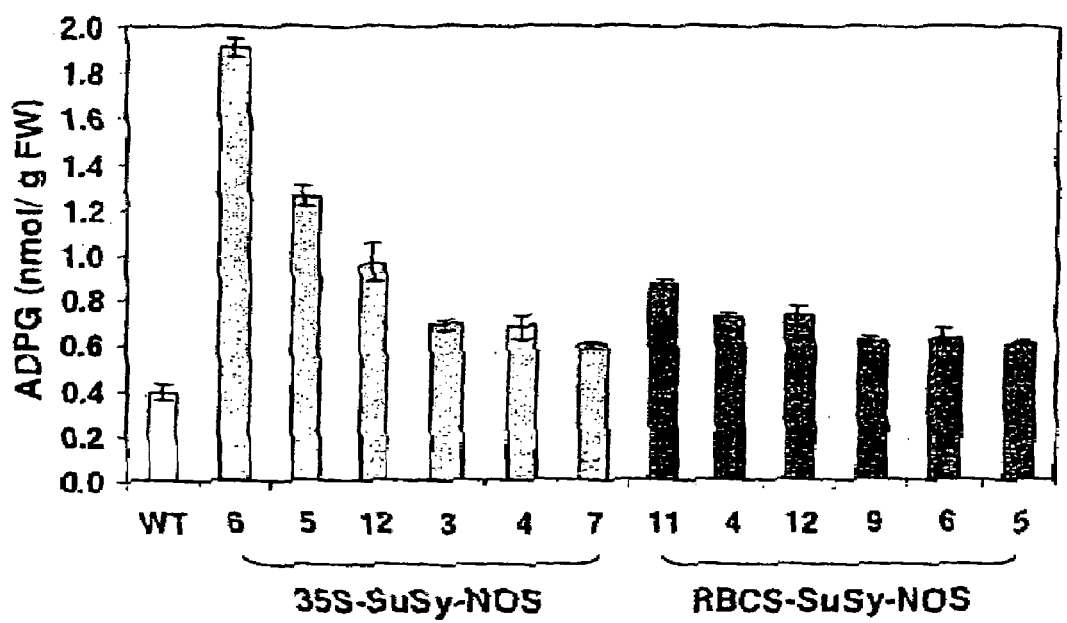

FIGS. 8-10 present the results obtained in leaves of potato plants that overexpress SS both constitutively (35S-SS-NOS), and specifically (RBCS-SS-NOS).

Figure 11:
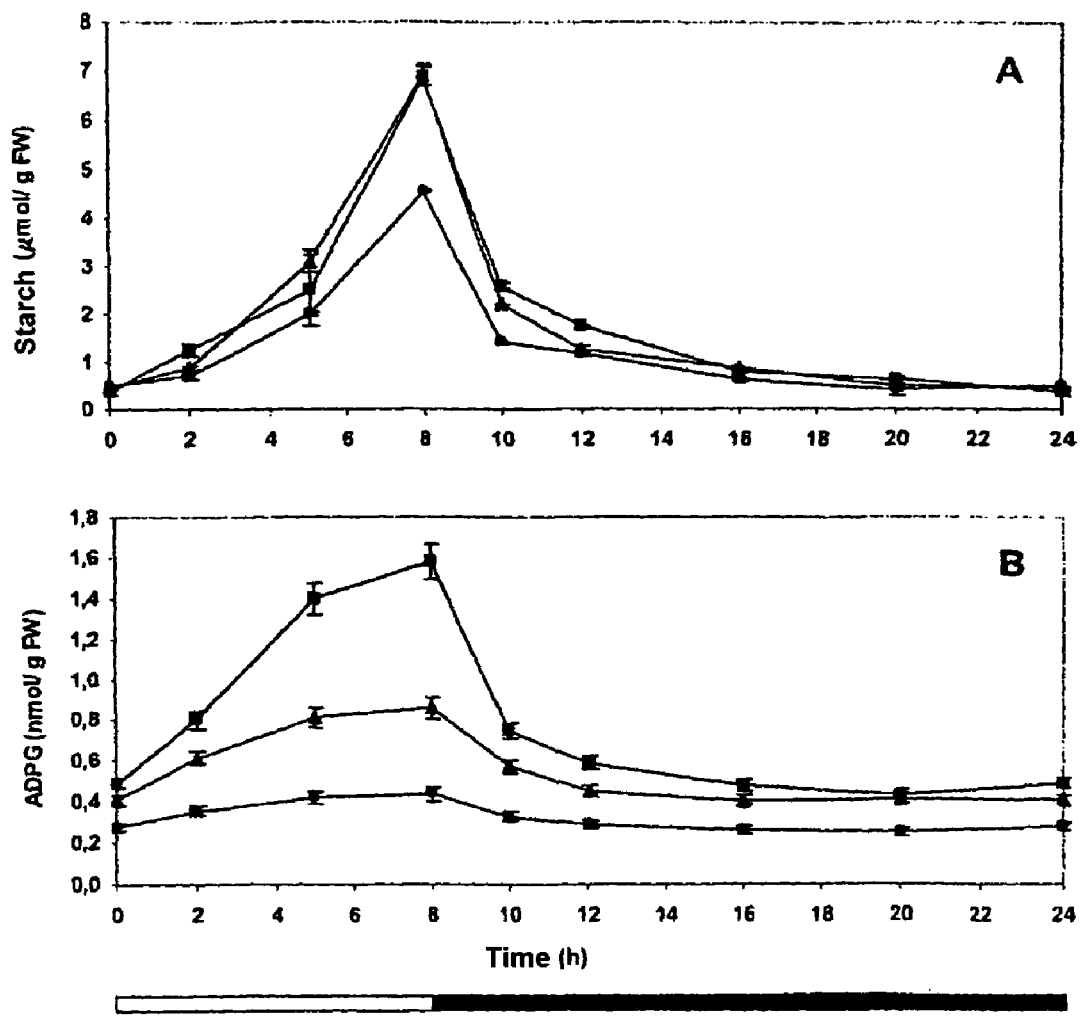

As shown in FIG. 8, the SS activity in the leaves of any of these plants is 2-10 times higher than in the same organ of a wild-type plant (WT). These leaves had the following characteristics:

1. Clear correlation between the ADPG-producing SS activity (FIG. 8) and levels of starch (FIG. 9) and ADPG (FIG. 10). This characteristic was observed not only in leaves, but also in storage tissues such as tubers and seeds (see below).
2. High starch content (FIG. 9) relative to leaves of wild-type plants. For example, the starch content of a leaf of a "wild-type" potato plant grown in a photoperiod of 8 hours light/16 hours darkness and at 20° C. is 5 micromol/gram of fresh weight, whereas a leaf of a transgenic plant that overexpresses SS is 8 micromol/gram fresh weight. The differences between wild-type and transgenic plants are accentuated when the photoperiod is long, so that the leaves of a plant that overexpresses SS contains 4 times more starch than those of a wild-type plant.
3. High ADPG content relative to the same tissue or organ of the untransformed plant (FIG. 10). The average content in a leaf of a wild-type potato plant grown in a photoperiod of 8 hours light/16 hours darkness and at 20° C. is 0.35 nanomol/gram of fresh weight, whereas the leaves of the plants that overexpress SS can have a content of 2.5 nanomol/gram of fresh weight.
4. Both ADPG and starch exhibit transitory accumulation over the photoperiod (FIG. 11). The rate of accumulation of both substances maintains a positive correlation with the SS activity, indicating that, contrary to what is suggested by the "classical" model of starch biosynthesis (FIG. 2A) and confirming the hypothesis of the "alternative" model shown in FIG. 2B, SS plays a fundamental role in the production of ADPG and in the link between sucrose metabolism and starch metabolism.
5. Normal levels of soluble sugars such as glucose and fructose. However, the levels of glucose-6-P and sucrose in transgenic leaves are higher than those observed in the wild-type potato leaves (Table 2).

TABLE 2

Levels of metabolites (expressed in nmol/g fresh weight) in leaves of control plants (WT) and 35S-SuSy-NOS source leaves. Values significantly different from those observed in WT are shown in bold.

|  | Control | 35S-SS-NOS | | | | | |
| --- | --- | --- | --- | --- | --- | --- | --- |
|  | WT | 6 | 5 | 12 | 3 | 4 | 7 |
| Glucose | 848 ± 31 | 922 ± 29 | 850 ± 30 | 933 ± 29 | 881 ± 56 | 895 ± 32 | 871 ± 60 |
| Fructose | 996 ± 43 | 1,035 ± 67 | 1,094 ± 17 | 1,022 ± 10 | 1067 ± 58 | 1078 ± 63 | 817 ± 41 |
| Sucrose | 1,012 ± 27 | 1,529 ± 48 | 1,402 ± 68 | 1,642 ± 58 | 1,307 ± 35 | 1,317 ± 35 | 1,391 ± 70 |
| Glucose-6-P | 244 ± 28 | 309 ± 15 | 280 ± 25 | 271 ± 27 | 355 ± 23 | 298 ± 12 | 315 ± 9.8 |
| Glucose-1-P | 22.7 ± 1.9 | 15.5 ± 2.1 | 10.3 ± 1.1 | 9.9 ± 1.2 | 9.5 ± 1.5 | 15.2 ± 1.9 | 11.4 ± 1.8 |

6. The external morphology of the plants that overexpress SS is not aberrant, when compared with that of the untransformed plants.

Figure 12:
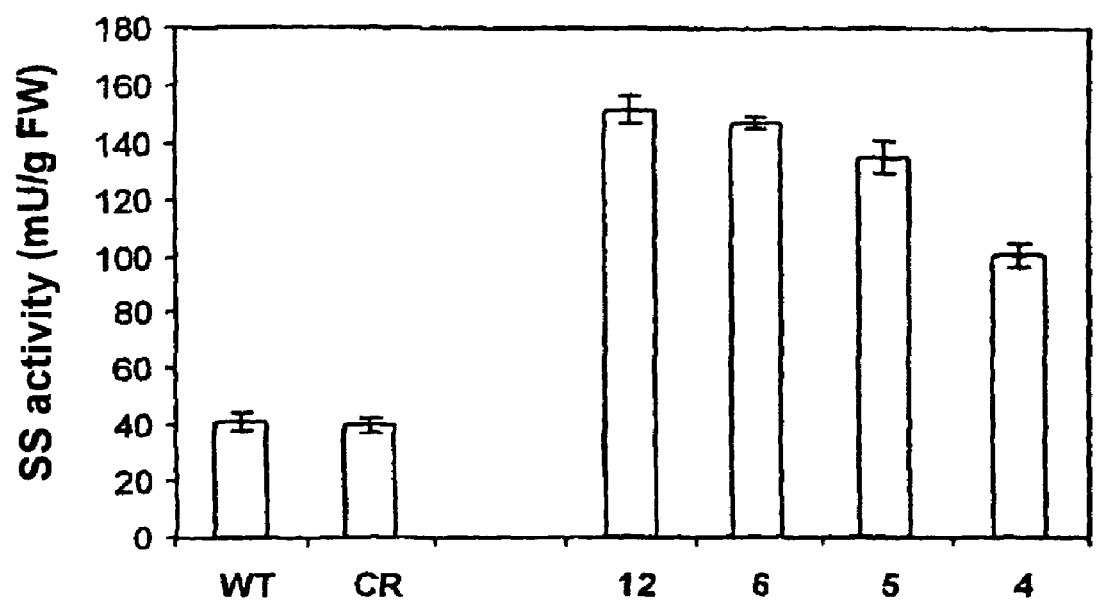
Figure 13:
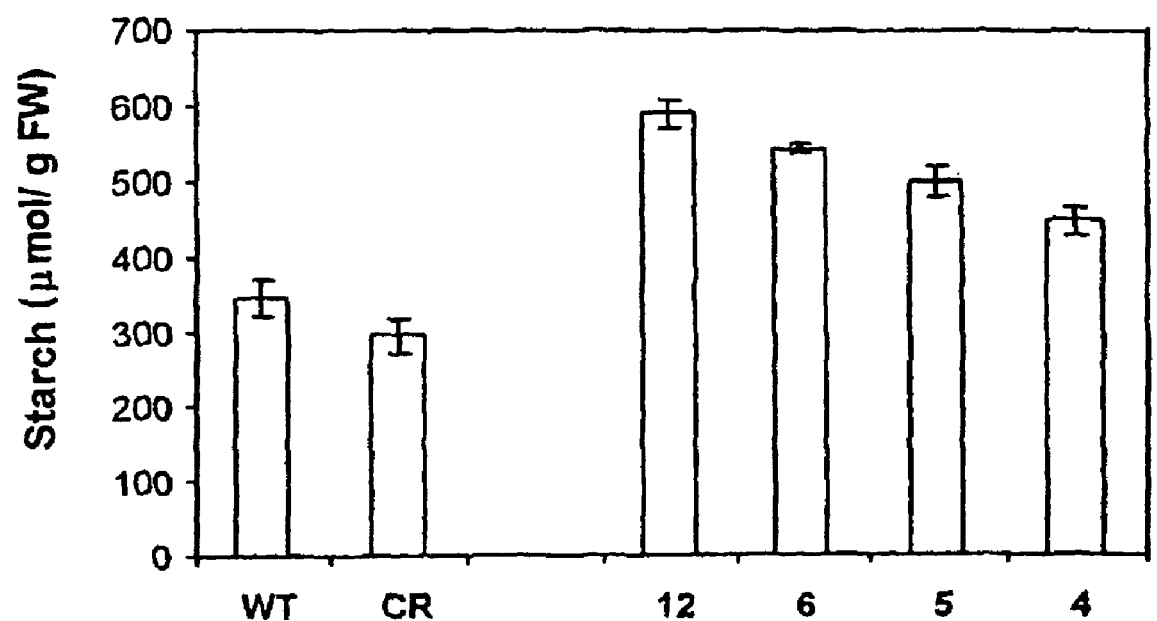
Figure 14:
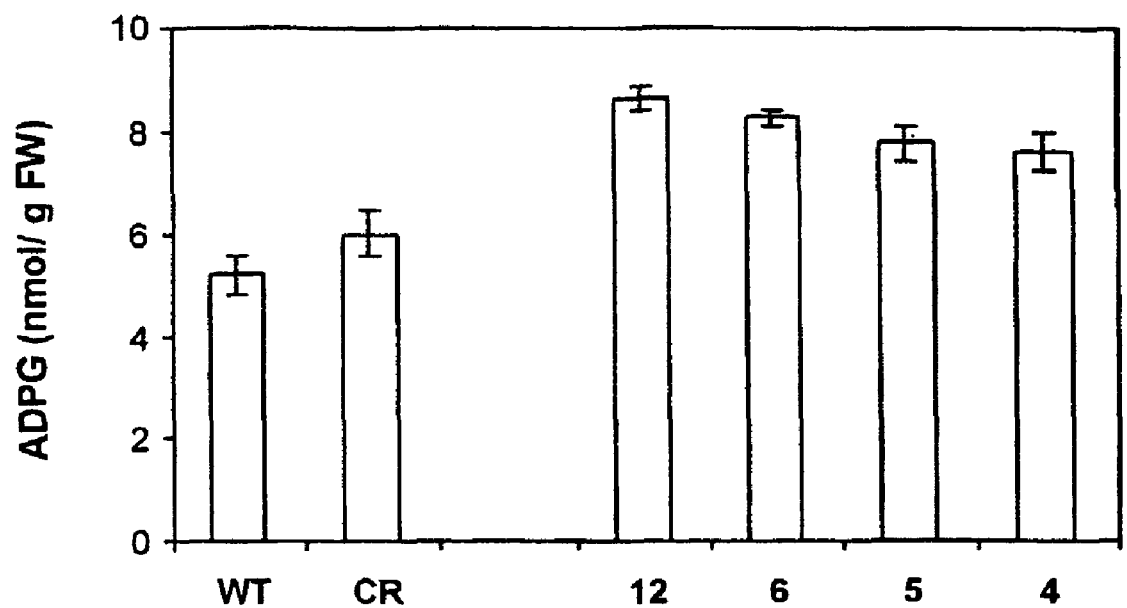

FIGS. 12-14 show the results obtained in potato tubers that overexpress SS constitutively (35S-SS-NOS). These results are essentially identical to those observed in tubers that overexpress SS under the control of a specific tuber promoter (promoter of the patatina gene).

As shown in FIG. 12, the SS activity in the tubers of any of these plants is ??? times greater than in the same organ of a wild-type plant. These tubers had the following characteristics:

1. Clear correlation between the ADPG-producing SS activity (FIG. 12) and levels of starch (FIG. 13) and ADPG (FIG. 14).
2. High starch content (FIG. 13) relative to tubers of untransformed plants. For example, the starch content in the tuber of the "wild-type" plant is approximately 300 micromol/gram of fresh weight (equivalent to 54 mg of starch/gram of fresh weight), whereas in a tuber that overexpresses SS it is 450-600 micromol/gram fresh weight.
3. High ADPG content relative to tubers of wild-type plants (FIG. 14). The average content in a wild-type tuber is 5 nanomol/gram of fresh weight, whereas the tubers that overexpress SS can have a content of 7-9 nanomol/gram of fresh weight.

The results obtained in rice seeds, tomato and tobacco leaves, as well as tomato fruits, are qualitatively similar to those shown in FIGS. 8-14. In all cases there was an increase in the content of starch and an increase in the amylose/amylbpectin ratio.

The production of plants with high content of ADPG and starch following overexpression of SS is a result that is totally unexpected according to the current ideas on the biosynthesis of starch (illustrated in FIGS. 1A and 2A) and perhaps explains why the design of plants that overexpress SS has not previously been adopted as a strategy for increasing starch production. The results obtained on the basis of this work suggest that SS, but not AGPase, is the fundamental source of ADPG that accumulates in plants. According to the models that are still current, AGPase is the only source of ADPG. Surprisingly, however, ADPG levels have never been investigated in AGPase-deficient plants. To explore the significance of our invention, we analysed the levels of ADPG and starch in *Arabidopsis* and potato plants with reduced AGPase activity for the first time. As shown in FIG. 15A, the levels of starch in AGPase-deficient TL25 *Arabidopsis* plants (Lin, T. P., Caspar, T., Somerville, C. R., Preiss, J. (1988) Isolation and characterization of a starchless mutant of *Arabidopsis thaliana* lacking ADPglucose pyrophosphorylase activity. Plant Physiol. 88, 1131-1135) are lower than those observed in the WT plants. However, the levels of ADPG are normal (FIG. 15B). In contrast, the levels of starch in AGP62 and AGP85 potato plants (Müller-Röber, B., Sonnewald, U. Willmitzer, L. (1992) Inhibition of the ADPglucose pyrophosphorylase in transgenic potatoes leads to sugar-storing tubers and influences tuber formation and expression of tuber storage protein genes. EMBO J. 11, 1229-1238) are reduced relative to those observed in leaves of wild-type plants (FIG. 16A). However, the levels of ADPG are completely normal (FIG. 16B). Taken together, these observations (a) show that SS, and not AGPase, is the principal source of ADPG in plants and (b) highlight the significance of our invention after demonstrating that overexpression of SS gives rise to plants with high starch content.

DESCRIPTION OF THE DIAGRAMS

FIG. 1: Mechanisms of starch biosynthesis in heterotrophic organs. (A) "Classical" mechanism according to which SS is involved in the production of UDPG, which is eventually converted to starch after the combined action of UDPG pyrophosphorylase (UGPase), cytosolic phosphoglucomutase (PGM), plastidial phosphoglucomutase, ADPG pyrophosphorylase (AGPase) and starch synthase. (B) "Alternative" mechanism according to which SS is involved in the direct production of ADPG in the cytosol. The ADPG is then transported to the amyloplast by the action of a translocator. Once inside the amyloplast, the starch synthase utilizes the ADPG for producing starch.

Figure 2:
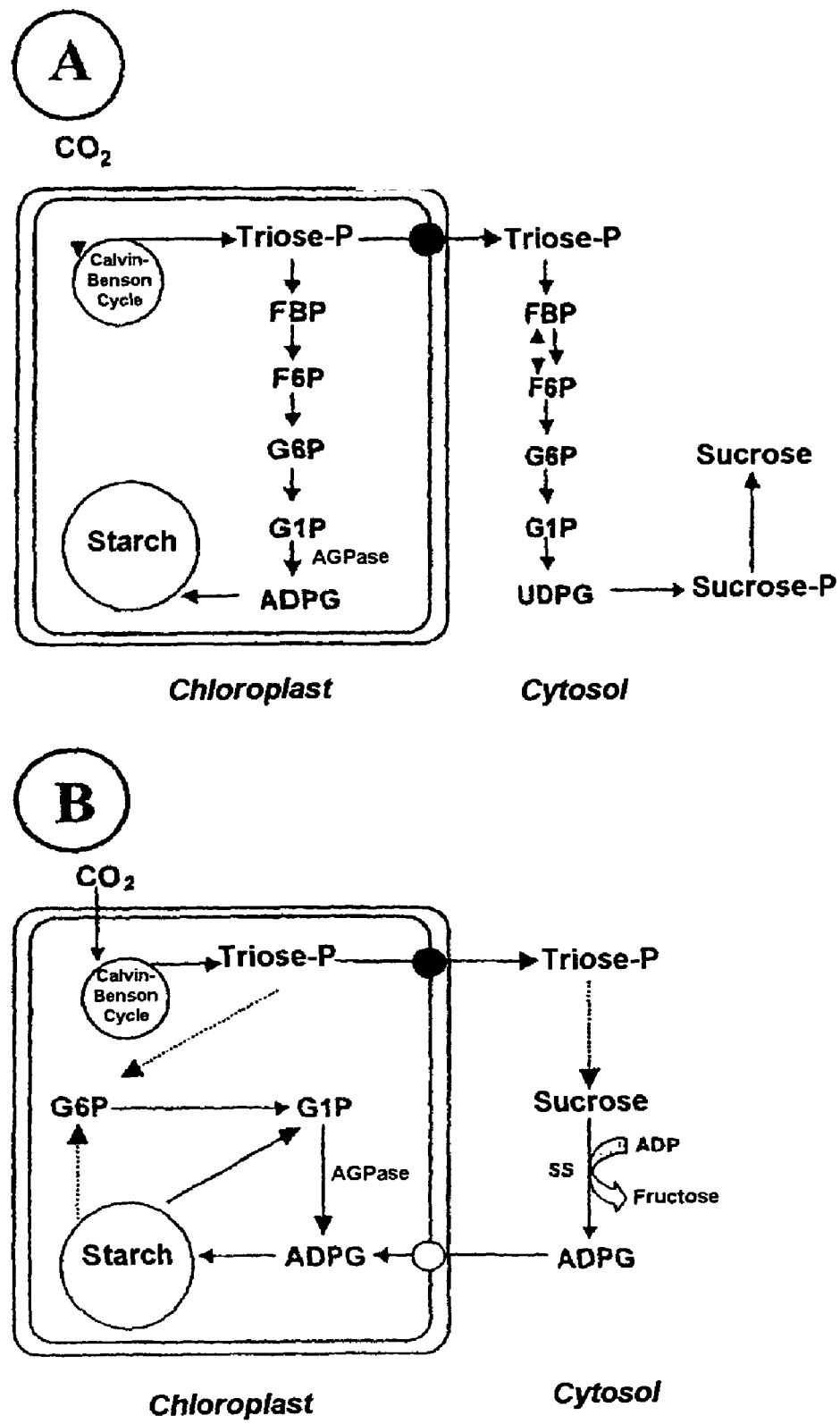

FIG. 2: Mechanisms of biosynthesis of starch in leaves. (A) "Classical" mechanism according to which the entire process of starch biosynthesis takes place inside the chloroplast. According to this view, starch metabolism and sucrose are not connected. Moreover, SS does not take part in the gluconeogenic process. (B) "Alternative" mechanism of starch biosynthesis according to which SS is involved in the direct synthesis of ADPG in the cytosol. The ADPG is then transported to the interior of the plastid where the starch synthase utilizes it as substrate for the reaction of starch synthesis.

FIG. 3: Stages in construction of the pET-SS expression plasmid from pET-28a(+) and pSS.

FIG. 4: Stages in construction of the pBIN35S-SS-NOS expression plasmid from pBIN20 and p35S-SS-NOS.

FIG. 5: Stages in construction of the pRBCS-SS-NOS expression plasmid from pGEMT-RBCSprom, p35S-SS-NOS and pBIN20.

FIG. 6: Expression of pET-SS in different strains of *Escherichia coli*. (A) SS activity (in milliunits (mU) per milligram of bacterial protein) in bacterial extracts transformed with pET or with pET-SS. The reaction took place in the direction of degradation of sucrose and production of ADPG. The reaction cocktail contained 50 mM HEPES (pH 7.0), 1 mM EDTA, 20% polyethylene glycol, 1 mM $MgCl_2$, 15 mM of KCl and 2 mM of ADP. Reaction took place for 10 minutes at 37° C. (B) SDS-PAGE of protein extracts from the various strains of *E. coli* transformed with pET and with pET-SS. The position of the recombinant SSX is indicated with an asterisk.

Figure 7:
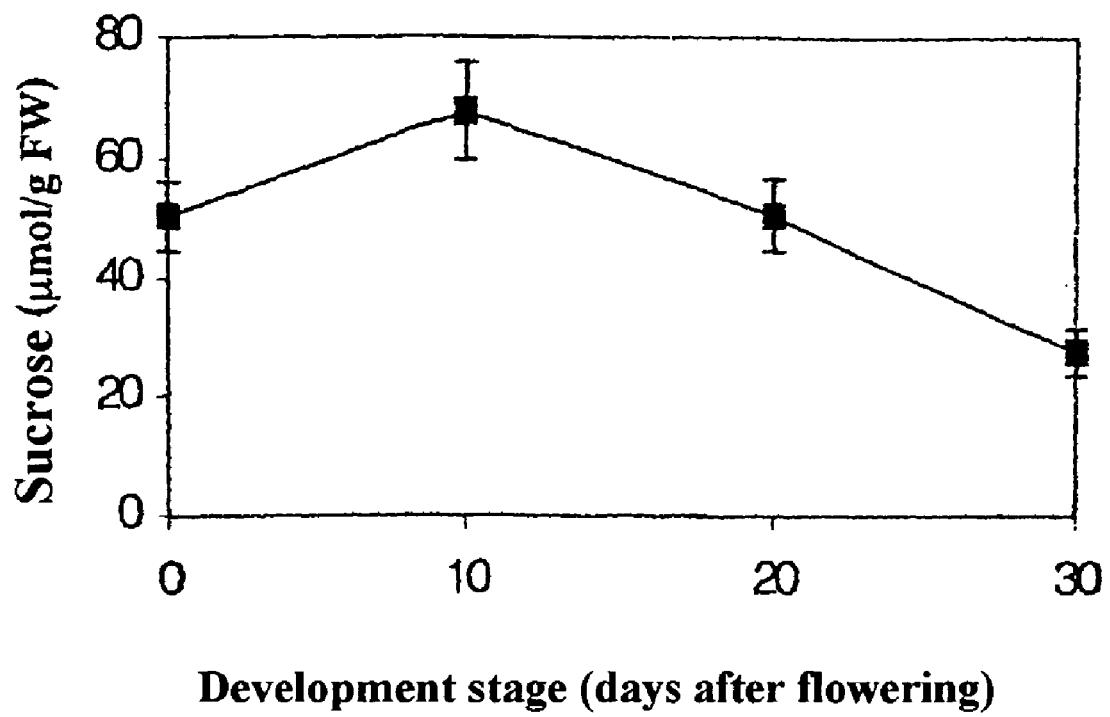

FIG. 7: Determination of sucrose at different stages of development of barley endosperm using the kit based on the coupled reactions of SS, ADPG (UDPG) pyrophosphatase, PGM and G6PDH. The results were identical to those obtained in parallel by (a) use of a kit based on the coupled reactions of SS and UDPG dehydrogenase and (b) use of high-performance chromatography (HPLC) with amperometric detection in a DX-500 Dionex system connected to a Carbo-Pac PA1 column.

Abscissa: Days after flowering
Ordinate: Sucrose content (μmol/gFW)

FIG. 8: SS activity in leaves of wild-type (WT) potato plants and potato plants that overexpress SSX following integration of the constructions 35S-SS-NOS (by the action of the strain of *Agrobacterium tumefaciens* CECT:5851) or RBCS-SS-NOS in their genome. Activity is expressed in milliunits (mU) per gram of fresh weight. The unit is defined as the amount of SS required for producing one micromol of ADPG per minute.

FIG. 9: Content of starch in leaves of wild-type (WT) potato plants and potato plants that overexpress SSX following integration of the constructions 35S-SS-NOS (by the action of the strain of *Agrobacterium tumefaciens* CECT: 5851) or RBCS-SS-NOS in their genome.

FIG. 10: Content of ADPG in leaves of wild-type (WT) potato plants and potato plants that overexpress SSX following integration of the constructions 35S-SS-NOS (by the action of the strain of *Agrobacterium tumefaciens* CECT: 5851) or RBCS-SS-NOS in their genome.

FIG. 11: Transitory accumulation of (A) starch and (B) ADPG during a photoperiod of 8 hours of light and 16 hours of darkness in leaves of WT plants (●), 35S-SS-NOS (■) and RBCS-SS-NOS (▲).

FIG. 12: SS activity (referred to fresh weight, FW) in tubers of wild-type potato plants (WT), regeneration controls (RG) and potato plants that overexpress SSX (lines 4, 5, 6 and 12) after integration of the construction 35S-SS-NOS in their genome (by the action of the strain of *Agrobacterium tumefaciens* CECT:5851). The activity is expressed in milliunits (mU) per gram of fresh weight. The unit is defined as the amount of SS required for producing one micromol of ADPG per minute.

FIG. 13: Content of starch (referred to fresh weight, FW) in tubers of wild-type potato plants (WT), regeneration controls (RG) and potato plants that overexpress SSX (lines 4, 5, 6 and 12) after integration of the construction 35S-SS-NOS in their genome (by the action of the strain of *Agrobacterium tumefaciens* CECT:5851).

FIG. 14: Content of ADPG (referred to fresh weight, FW) in tubers of wild-type potato plants (WT) and potato plants that overexpress SSX after integration of the construction 35S-SS-NOS in their genome (by the action of the strain of *Agrobacterium tumefaciens* CECT:5851).

Figure 15:
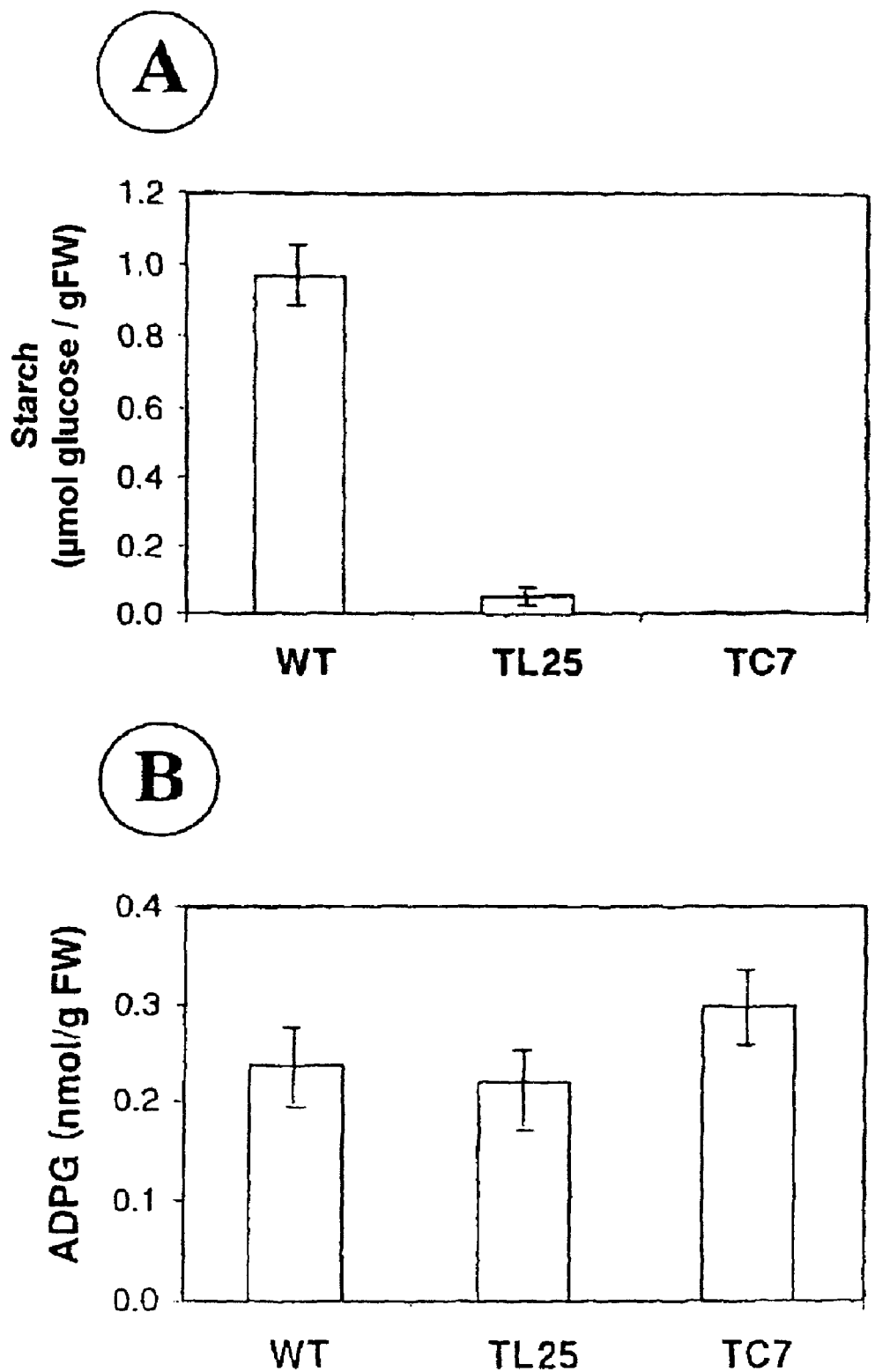

FIG. 15: Content of (A) starch and (B) ADPG in leaves of AGPase-deficient *Arabidopsis thaliana* TL25.

Figure 16:
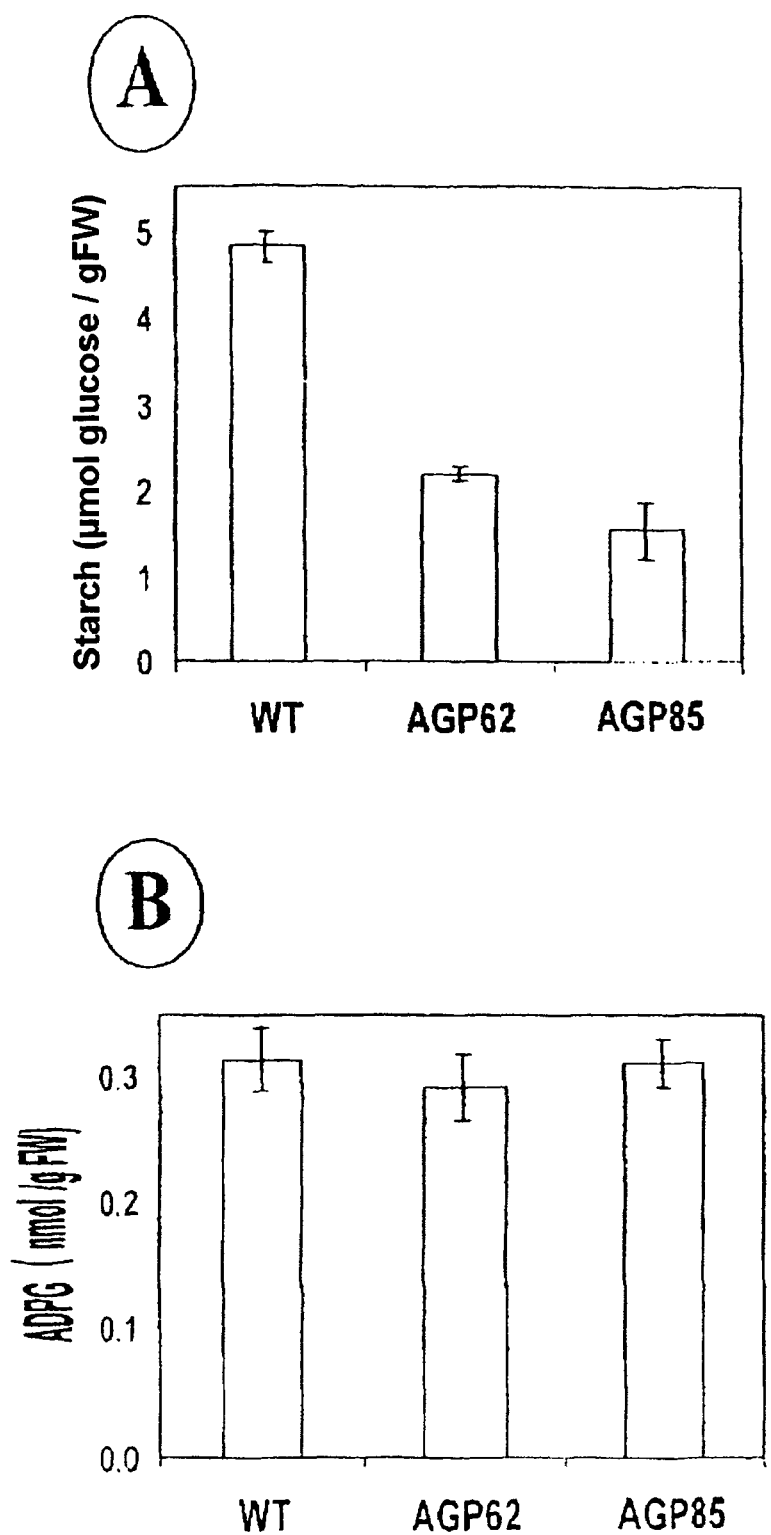

FIG. 16: Content of (A) starch and (B) ADPG in leaves of AGPase-deficient potato AGP62 and AGP85.

The invention claimed is:

1. An isolated peptide comprising the sucrose synthase of SEQ ID NO: 12.

2. The isolated peptide as claimed in claim 1 that consists of SEQ ID NO: 12.

3. A method of preparing ADPG comprising the steps of incubating the isolated peptide of claim 1 with ADP in suitable conditions for causing a reaction that produces ADPG followed by isolation and purification of the ADPG produced.

4. The method of preparing ADPG according to claim 3, comprising the steps of:
 a) Providing 100 ml of the following solution for the incubating step and incubating for 12 h at 37° C.:

| Sucrose | 1 M |
|---|---|
| HEPES, pH 7.0 | 50 mM |
| EDTA | 1 mM |
| Polyethylene glycol | 20% |
| $MgCl_2$ | 1 mM |
| KCl | 15 mM |
| ADP | 100 mM | b) Stopping the reaction by heating,
 c) Centrifuging at 10000 g for 10 min with formation of a supernatant, and
 d) Chromatographing the supernatant by HPLC, and then eluting and purifying the ADPG.

5. An assay kit for the spectrophotometric, fluorimetric or amperometric determination of sucrose comprising the sucrose synthase of claim 1.

6. The assay kit as claimed in claim 5, comprising an incubation medium with the following components:
 a) 2 units of sucrose synthase,
 b) 2 mM of ADP
 c) 2 units of ADPG pyrophosphatase of plant, animal or microbial origin
 d) 2 units of PGM
 e) 2 units of G6PDH
 f) 0.5 mM of NAD(P)
 g) 100 ml of reaction buffer: 50 mM HEPES, pH 7.0/1 mM EDTA/20% polyethylene glycol/1 mM $MgCl_2$/15 mM KCl
 h) Previously filtered test sample.

7. The assay kit as claimed in claim 5, comprising an incubation medium with the following components:
 a) 2 units of sucrose synthase,
 b) 2 mM of UDP
 c) 2 units of UDPG pyrophosphatase of plant, animal or microbial origin
 d) 2 units of PGM
 e) 2 units of G6PDH
 f) 0.5 mM of NAD(P)
 g) 100 ml of reaction buffer: 50 mM HEPES, pH 7.0/1 mM EDTA/20% polyethylene glycol/1 mM $MgCl_2$ /5 mM KCl
 h) Previously filtered test sample.

8. The assay kit as claimed in claim 5, comprising an incubation medium with the following components:
 a) 2 units of sucrose synthase,
 b) 2 mM of UDP
 c) 2 units of UDPG dehydrogenase
 d) 0.5 mM of NAD
 e) 100 ml of reaction buffer: 50 mM HEPES, pH 7.0/1 mM EDTA/20% polyethylene glycol/1 mM $MgCl_2$ /15 mM KCl
 f) Previously filtered test sample.

9. A method of producing a transgenic plant that overexpresses sucrose synthase comprising the steps of inserting a genetic construct that contains and expresses the DNA fragment of SEQ ID NO: 11 in a suitable vector and transferring the genetic construction to the genome of a plant.

10. The method according to claim 9, wherein the vector comprises pSS5.

11. A transgenic plant comprising a genetic construct that overexpresses a sucrose synthase comprising SEQ ID NO: 12 such that the plant has a higher content of sucrose, G6P, ADPG and starch than a corresponding wild-type plant without the genetic construct.

12. The transgenic plant according to claim 11, wherein the transgenic plant has a level of sucrose synthase enzyme activity that is 2-10 times greater than a level of sucrose synthase enzyme activity in a corresponding wild-type plant without the genetic construct.

13. The transgenic plant according to claim 11, which is selected from the group consisting of a tobacco plant, a potato plant a tomato plant and a rice plant.

14. The transgenic plant according to claim 12, which is selected from the group consisting of a tobacco plant, a potato plant a tomato plant and a rice plant.

15. The transgenic plant according to claim 13, wherein the plant has leaves with a content of sucrose, G6P, ADPG and starch and with an amylose/amylopectin ratio that is higher than those in leaves of a corresponding wild-type plant.

16. The transgenic plant according to claim 14, wherein the plant has leaves with a content of sucrose, G6P, ADPG and starch and with an amylose/amylopectin ratio that is higher than those in leaves of a corresponding wild-type plant.

17. The transgenic plant according to claim 13, wherein the plant has at least one of a root, tuber or seed with a content of sucrose, G6P, ADPG and starch and with an amylose/amylopectin ratio that is higher than those in a root, tuber or seed of a corresponding wild-type plant.

18. The transgenic plant according to claim 13, wherein the plant has at least one of a root, tuber or seed with a content of sucrose, G6P, ADPG and starch and with an amylose/amylopectin ratio that is higher than those in a root, tuber or seed of a corresponding wild-type plant.

* * * * *

UNITED STATES PATENT AND TRADEMARK OFFICE
CERTIFICATE OF CORRECTION

PATENT NO.       : 8,168,856 B2                              Page 1 of 1
APPLICATION NO.  : 10/587372
DATED            : May 1, 2012
INVENTOR(S)      : Miren Edurne Baroja Fernandez et al.

It is certified that error appears in the above-identified patent and that said Letters Patent is hereby corrected as shown below:

Col. 38, line 4, Claim 18 is cancelled.

Signed and Sealed this
Twelfth Day of June, 2012

David J. Kappos
*Director of the United States Patent and Trademark Office*

UNITED STATES PATENT AND TRADEMARK OFFICE
CERTIFICATE OF CORRECTION

| | | |
|---|---|---|
| PATENT NO. | : 8,168,856 B2 | |
| APPLICATION NO. | : 10/587372 | |
| DATED | : May 1, 2012 | |
| INVENTOR(S) | : Miren Edurne Baroja Fernandez et al. | |

It is certified that error appears in the above-identified patent and that said Letters Patent is hereby corrected as shown below:

Delete the title page and substitute therefore the attached title page showing the corrected number of claims in patent.

Column 38, lines 4-8, delete claim 18.

This certificate supersedes the Certificate of Correction issued June 12, 2012.

Signed and Sealed this
Third Day of July, 2012

David J. Kappos
*Director of the United States Patent and Trademark Office*

(12) United States Patent
Baroja Fernandez et al.

(10) Patent No.: US 8,168,856 B2
(45) Date of Patent: May 1, 2012

(54) METHOD OF PRODUCTION OF RECOMBINANT SUCROSE SYNTHASE, USE THEREOF IN THE MANUFACTURE OF KITS FOR DETERMINATION OF SUCROSE, PRODUCTION OF ADPGLUCOSE AND PRODUCTION OF TRANSGENIC PLANTS WHOSE LEAVES AND STORAGE ORGANS ACCUMULATE HIGH CONTENTS OF ADPGLUCOSE AND STARCH

(75) Inventors: Miren Edurne Baroja Fernandez, Edificio el Sario (ES); Francisco José Muñoz Perez, Edificio el Sario (ES); Francisco Javier Pozueta Romero, Edificio el Sario (ES); Maria Teresa Moran Zorzano, Edificio el Sario (ES); Nora Alonso Casajus, Edificio el Sario (ES)

(73) Assignees: Universidad Publica de Navarra, Pamplona, Navarra (ES); Consejo Superior de Investigaciones Cientificas, Madrid (ES)

( * ) Notice: Subject to any disclaimer, the term of this patent is extended or adjusted under 35 U.S.C. 154(b) by 962 days.

(21) Appl. No.: 10/587,372

(22) PCT Filed: Jan. 27, 2005

(86) PCT No.: PCT/ES2005/070010
§ 371 (c)(1),
(2), (4) Date: Jun. 12, 2008

(87) PCT Pub. No.: WO2005/075649
PCT Pub. Date: Aug. 18, 2005

(65) Prior Publication Data
US 2009/0288219 A1 Nov. 19, 2009

(30) Foreign Application Priority Data
Feb. 5, 2004 (ES) ................... 200400257

(51) Int. Cl.
*A01H 5/00* (2006.01)
*C12N 15/82* (2006.01)
*C12N 15/00* (2006.01)
*C12N 15/10* (2006.01)

(52) U.S. Cl. ............... 800/278; 800/295; 435/320.1; 435/468; 536/23.1; 536/23.6

(58) Field of Classification Search ............ None
See application file for complete search history.

(56) References Cited

U.S. PATENT DOCUMENTS
2003/0135870 A1 * 7/2003 Cheikh et al. ................. 800/8

FOREIGN PATENT DOCUMENTS
| WO | 94/28146 | 12/1994 |
| WO | 98/03637 | 1/1998 |
| WO | 99/10511 | 3/1999 |
| WO | 02/45485 | 6/2002 |
| WO | 02/067662 | 9/2002 |

OTHER PUBLICATIONS

Zrenner et al 1995 The Plant Journal 7:97-107.*
Baroja-Fernandez et al 2003 Plant Cell Physiology 44:500-509, provided by Applicant.*
E. Baroja-Fernández, et al; "Sucrose Synthase Catalyzes the de novo Production of ADPglucose Linked to Starch Biosynthesis in Heterotrophic Tissues of Plants"; *Plant Cell Physiol* (2003) 44(5) pp. 500-509.
R. Zrenner, et al; Evidence of the crucial role of sucrose synthase for sink strength using transgenic potato plants (*Solanum tuberosum* L.); *The Plant Journal* (1995); 7(1) pp. 97-107.
J. Pozueta-Romero, et al; "ADPG formation by the ADP-specific cleavage of sucrose-reassessment of sucrose synthase"; *Federation of European Biochemical Societies* (1991) ADONIS 001457939101000I.; vol. 291, No. 2; pp. 233-237.
P.S. Chourey et al; "Genetic evidence that the two isozymes of sucrose synthase present in developing maize endosperm are critical, one for cell wall integrity and the other for starch biosynthesis"; *Mol Gen Genet* (1998) 259; pp. 88-96.
M. Salanoubat et al; Molecular cloning and sequencing of sucrose synthase cDNA from potato (*Solanum tuberosum* L.): preliminary characterization of sucrose synthase mRNA distribution; *Gene* (1987) 60 pp. 47-56.
T. Nakai, et al; "Expression and Characterization of Sucrose Synthase from Mung Bean Seedlings in *Escherichia coli*"; *Biosci Biotech. Biochem* (1997) 61 (9), pp. 1500-1503.
T. Nakai, et al; "An Increase in Apparent Affinity for Sucrose of Mung Bean Sucrose Synthase Is Caused by In Vitro Phosphorylation or Directed Mutagenesis if Ser"; *Plant Cell Physiol* (1998) 39(12); pp. 1337-1341.

* cited by examiner

*Primary Examiner* — Brent T Page
(74) *Attorney, Agent, or Firm* — Ladas & Parry LLP

(57) ABSTRACT

An isolated sucrose synthase peptide. Also, a method of preparing ADPglucose by incubating the isolated sucrose synthase peptide with ADP in suitable conditions and then isolating and purifying the ADPG produced. Also, an assay kit for the spectrophotometric, fluorimetric or amperometric determination of sucrose, which kit includes the isolated sucrose synthase peptide. Also, a method of producing a transgenic plant that overexpresses sucrose synthase by inserting a genetic construct containing a DNA fragment that encodes the sucrose synthase peptide into a vector and transferring to a plant genome, and a transgenic plant obtained thereby.

17 Claims, 22 Drawing Sheets